US011523834B1

(12) United States Patent
Evans et al.

(10) Patent No.: US 11,523,834 B1
(45) Date of Patent: Dec. 13, 2022

(54) CARTILAGE AND BONE HARVEST AND DELIVERY SYSTEM AND METHODS

(71) Applicant: University of Utah Research Foundation, Salt Lake City, UT (US)

(72) Inventors: Zackery Evans, Woods Cross, UT (US); T. Wade Fallin, Hyde Park, UT (US); Travis G. Maak, Park City, UT (US); Charles L. Saltzman, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 17/844,149

(22) Filed: Jun. 20, 2022

(51) Int. Cl.
*A61B 17/16* (2006.01)
(52) U.S. Cl.
CPC .................. *A61B 17/1635* (2013.01)
(58) Field of Classification Search
CPC ................. A61B 17/1635; A61F 2/4618
See application file for complete search history.

(56) References Cited

U.S. PATENT DOCUMENTS

| | | | |
|---|---|---|---|
| 1,493,240 | A | 5/1924 | Bohn |
| 2,919,692 | A | 1/1960 | Wolfgang |
| 4,069,824 | A | 1/1978 | Weinstock |
| 4,649,918 | A | 3/1987 | Pegg |
| 4,696,308 | A | 9/1987 | Meller et al. |
| 4,782,833 | A | 11/1988 | Einhorn |
| 4,913,143 | A | 4/1990 | Oloff |
| 5,197,967 | A | 3/1993 | Wilson |
| 5,330,480 | A | 7/1994 | Meloul |
| 5,346,497 | A | 9/1994 | Simon |
| 5,423,823 | A | 6/1995 | Schmieding |
| 5,556,399 | A | 9/1996 | Huebner |

(Continued)

FOREIGN PATENT DOCUMENTS

WO WO2011026164 A1 3/2011

OTHER PUBLICATIONS

Anthrex, IntraOsseous BioPlasty® (IOBP®) Surgical Technique for a Bone Marrow Lesion of the Hip, https://www.arthrex.com/resources/animaton/PyHgVtD0Ui-OgF7h3PoIw/intraosseous-bioplasty-jobp-surgical-technique-for-a-bone-marrow-lesion-of-the-hip, accessed on or before Mar. 28, 2022.

(Continued)

*Primary Examiner* — Andrew Yang
(74) *Attorney, Agent, or Firm* — David Meibos; Maywood IP Law

(57) ABSTRACT

A system for harvesting bone material from a bone may include a rotary cutter defining a rotary cutter longitudinal axis extending between a rotary cutter proximal end and a rotary cutter distal end. The rotary cutter may have a drive shaft configured to receive input torque, and an osteochondral cutter configured to cut the tissue and receive the tissue material in response to rotation of the osteochondral cutter under pressure against the tissue. The system may further include a bone port defining a bone port longitudinal axis extending between a bone port proximal end and a bone port distal end. The bone port may have a bone port cannulation sized to closely fit over the osteochondral cutter. At least one of the bone port proximal end and the bone port distal end may be securable to the tissue. A stratiform tissue graft may be delivered through the bone port.

11 Claims, 26 Drawing Sheets

(56) References Cited

U.S. PATENT DOCUMENTS

| | | | |
|---|---|---|---|
| 5,782,835 A | 7/1998 | Hart | |
| 5,885,293 A | 3/1999 | McDevitt | |
| 5,919,196 A | 7/1999 | Bobic | |
| 5,928,238 A | 7/1999 | Scarborough | |
| 6,017,348 A | 1/2000 | Hart | |
| 6,110,209 A | 8/2000 | Stone | |
| 6,146,385 A * | 11/2000 | Torrie | A61F 2/4601 606/88 |
| 6,193,722 B1 | 2/2001 | Zech | |
| 6,200,319 B1 | 3/2001 | Storer | |
| 6,358,253 B1 | 3/2002 | Torrie | |
| 6,395,011 B1 | 5/2002 | Johanson | |
| 6,591,581 B2 | 7/2003 | Schmieding | |
| 6,592,588 B1 | 7/2003 | Bobic | |
| 6,607,561 B2 | 8/2003 | Brannon | |
| 6,682,535 B2 | 1/2004 | Hoogland | |
| 6,767,354 B2 | 7/2004 | Johanson | |
| 6,857,520 B2 | 2/2005 | Salazar | |
| 6,884,245 B2 | 4/2005 | Spranza, III | |
| 6,942,669 B2 | 9/2005 | Kure | |
| 7,445,595 B2 | 11/2008 | Brannon | |
| 7,513,901 B2 | 4/2009 | Seifert | |
| 7,537,597 B2 | 5/2009 | Salazar | |
| RE40,796 E | 6/2009 | O'Neill | |
| 7,591,820 B2 * | 9/2009 | Schmieding | A61B 17/1635 606/79 |
| 7,819,888 B2 | 10/2010 | Johanson | |
| 7,824,711 B2 | 11/2010 | Kizer | |
| 7,879,040 B2 | 2/2011 | Bharadwaj | |
| 8,043,315 B2 | 10/2011 | Shepard | |
| 8,162,967 B1 | 4/2012 | Kaiser | |
| 8,221,423 B2 | 7/2012 | Gil | |
| 8,251,998 B2 | 8/2012 | Hoeppner | |
| 8,382,762 B2 | 2/2013 | Brannon | |
| 8,414,585 B2 | 4/2013 | Meneghini | |
| 8,497,121 B2 | 7/2013 | Yao | |
| 8,518,433 B2 | 8/2013 | Kizer | |
| 8,777,956 B2 | 7/2014 | Hoeppner | |
| 8,801,716 B2 | 8/2014 | Meridew | |
| 8,814,882 B2 | 8/2014 | Oostman, Jr. et al. | |
| 8,845,644 B1 | 9/2014 | Verhoogen | |
| 8,998,918 B2 | 4/2015 | Jamali | |
| 9,084,465 B2 | 7/2015 | Oostman, Jr | |
| 9,119,646 B2 | 9/2015 | Sharkey | |
| 9,186,380 B2 | 11/2015 | Shi | |
| 9,393,062 B2 | 7/2016 | O'Halloran | |
| 9,532,876 B2 | 1/2017 | Sharkey | |
| 9,572,686 B2 | 2/2017 | Meridew | |
| 9,707,081 B2 | 7/2017 | Sharkey | |
| 9,757,135 B1 | 9/2017 | Kelley | |
| 9,782,196 B2 | 10/2017 | Bradica | |
| 9,855,393 B2 | 1/2018 | Schmieding | |
| 9,901,355 B2 | 2/2018 | Bourque | |
| 9,913,721 B2 | 3/2018 | Sharkey | |
| 9,925,068 B2 | 3/2018 | Bays et al. | |
| 9,937,057 B2 | 4/2018 | Gage | |
| 10,058,369 B2 | 8/2018 | O'Halloran | |
| 10,130,343 B2 | 11/2018 | Miller | |
| 10,159,470 B2 | 12/2018 | McWeeney | |
| 10,231,846 B2 | 3/2019 | Popejoy | |
| 10,300,170 B2 | 5/2019 | Masinaei | |
| 10,524,775 B2 | 1/2020 | Benedict | |
| 10,548,693 B2 | 2/2020 | Wang | |
| 10,687,880 B2 | 6/2020 | DeRidder | |
| 10,729,549 B2 | 8/2020 | Schmieding | |
| 10,857,001 B2 | 12/2020 | Popejoy | |
| 10,912,573 B2 | 2/2021 | Sweitzer | |
| 10,945,776 B2 | 3/2021 | Elser | |
| 10,973,532 B2 | 4/2021 | Miller | |
| 11,020,244 B2 | 6/2021 | Bays | |
| 11,039,871 B2 | 6/2021 | Lee | |
| 11,090,032 B2 | 8/2021 | Miller | |
| 11,116,646 B2 | 9/2021 | Greenhalgh et al. | |
| 11,185,339 B2 | 11/2021 | Perez | |
| 2002/0010471 A1 | 1/2002 | Wironen | |
| 2002/0099382 A1 | 7/2002 | Salazar | |
| 2003/0055431 A1 | 3/2003 | Brannon | |
| 2004/0030343 A1 | 2/2004 | Kure | |
| 2004/0034359 A1 | 2/2004 | Schmieding | |
| 2004/0034437 A1 | 2/2004 | Schmieding | |
| 2004/0210246 A1 | 10/2004 | Johanson | |
| 2005/0131313 A1 | 6/2005 | Mikulka et al. | |
| 2005/0196460 A1 | 9/2005 | Malinin | |
| 2006/0173476 A1 | 8/2006 | Bradica et al. | |
| 2006/0195122 A1 | 8/2006 | Vibe-Hansen | |
| 2007/0043376 A1 * | 2/2007 | Leatherbury | A61B 17/1635 606/99 |
| 2007/0123892 A1 | 5/2007 | Ries | |
| 2007/0270711 A1 | 11/2007 | Gil | |
| 2008/0167652 A1 | 7/2008 | Reinhard | |
| 2008/0262616 A1 * | 10/2008 | McKay | A61F 2/28 623/14.12 |
| 2008/0269895 A1 | 10/2008 | Steinwachs et al. | |
| 2009/0054906 A1 * | 2/2009 | Walthall | A61F 2/4618 606/108 |
| 2009/0149707 A1 | 6/2009 | Brannon | |
| 2009/0209964 A1 | 8/2009 | Yeung | |
| 2009/0274996 A1 | 11/2009 | Miller | |
| 2010/0094361 A1 | 4/2010 | Meneghini | |
| 2011/0177472 A1 | 7/2011 | Lee | |
| 2011/0306983 A1 | 12/2011 | O'Halloran | |
| 2012/0045731 A1 | 2/2012 | Singh | |
| 2012/0053641 A1 | 3/2012 | Meridew | |
| 2012/0237558 A1 | 9/2012 | Kizer | |
| 2013/0098942 A1 | 4/2013 | Greter | |
| 2013/0144292 A1 | 6/2013 | To | |
| 2013/0144295 A1 | 6/2013 | To | |
| 2013/0144320 A1 | 6/2013 | To | |
| 2014/0074103 A1 | 3/2014 | Mandeen | |
| 2014/0088712 A1 | 3/2014 | Gage | |
| 2014/0309641 A1 | 10/2014 | Bourque | |
| 2014/0350585 A1 | 11/2014 | Meridew | |
| 2014/0358170 A1 | 12/2014 | To et al. | |
| 2016/0066946 A1 | 3/2016 | To et al. | |
| 2017/0143351 A1 | 5/2017 | Devitre | |
| 2018/0104062 A1 | 4/2018 | Chen | |
| 2018/0110531 A1 | 4/2018 | Arthurs | |
| 2018/0147071 A1 | 5/2018 | Budyansky | |
| 2019/0117403 A1 | 4/2019 | Schmieding | |
| 2019/0290439 A1 | 9/2019 | Marionneaux | |
| 2019/0298482 A1 | 10/2019 | Hensler | |
| 2019/0328548 A1 | 10/2019 | Bake | |
| 2019/0388100 A1 | 12/2019 | Perez | |
| 2020/0100800 A1 | 4/2020 | Seykora | |
| 2020/0121463 A1 | 4/2020 | Yoshikawa | |
| 2020/0188556 A1 | 6/2020 | Kelly | |
| 2020/0275963 A1 | 9/2020 | Schlachter | |
| 2020/0275965 A1 | 9/2020 | DeRidder | |
| 2020/0330080 A1 | 10/2020 | Brewer | |
| 2020/0360068 A1 | 11/2020 | Dewey | |
| 2021/0282940 A1 | 9/2021 | Bays | |

OTHER PUBLICATIONS

Anthrex, Illiac Crest Bone Graft Harvesting Surgical Technique, https://www.arthrex.com/resources/surgical-technigue-guide/1Mt9Lft52k-pnwFD9v67TA/iliac-crest-bone-graft-harvesting, accessed on or before Mar. 28, 2022.

Anthrex, Autograft OATS 2.0 Set Surgical Technique, https://www.arthrex.com/resources/surgical-technique-guide/sjkOfkEEeCRTQBQVoRHOw/autograft-oats-20-set, accessed on or before Mar. 28, 2022.

Fanelli, ACL Revision Using Revision Dowels and Demineralized Cortical Fibers, CONMED, Nov. 18, 2013, https://www.youtbe.com/watch? =-156M492rVQ.

Becton Dickinson, Jamshidi Bone Marrow Biopsy Needles Overview, https://www.bd.com/en-us/resource-and-education/doeumentation-landing-page?heroSearchValue=Jamshidi%20overview&lastUpdate=all dates, accessed on or before Mar. 28, 2022.

Knight, Vexim Rebalancing Spine, Animation of the Spine Jack Technique for the reconstruction of osteoporotic vertebral fractures, May 11, 2014, https://www.youtube.com/watch?v=y0iUcGIRD_0.

(56) References Cited

OTHER PUBLICATIONS

APEX iTool, APEXAVN, Avascular necrosis https://www.apexitooloet/PRODUCTS-xq?_1=en&product_id=65, accessed on or before Mar. 28, 2022.

* cited by examiner

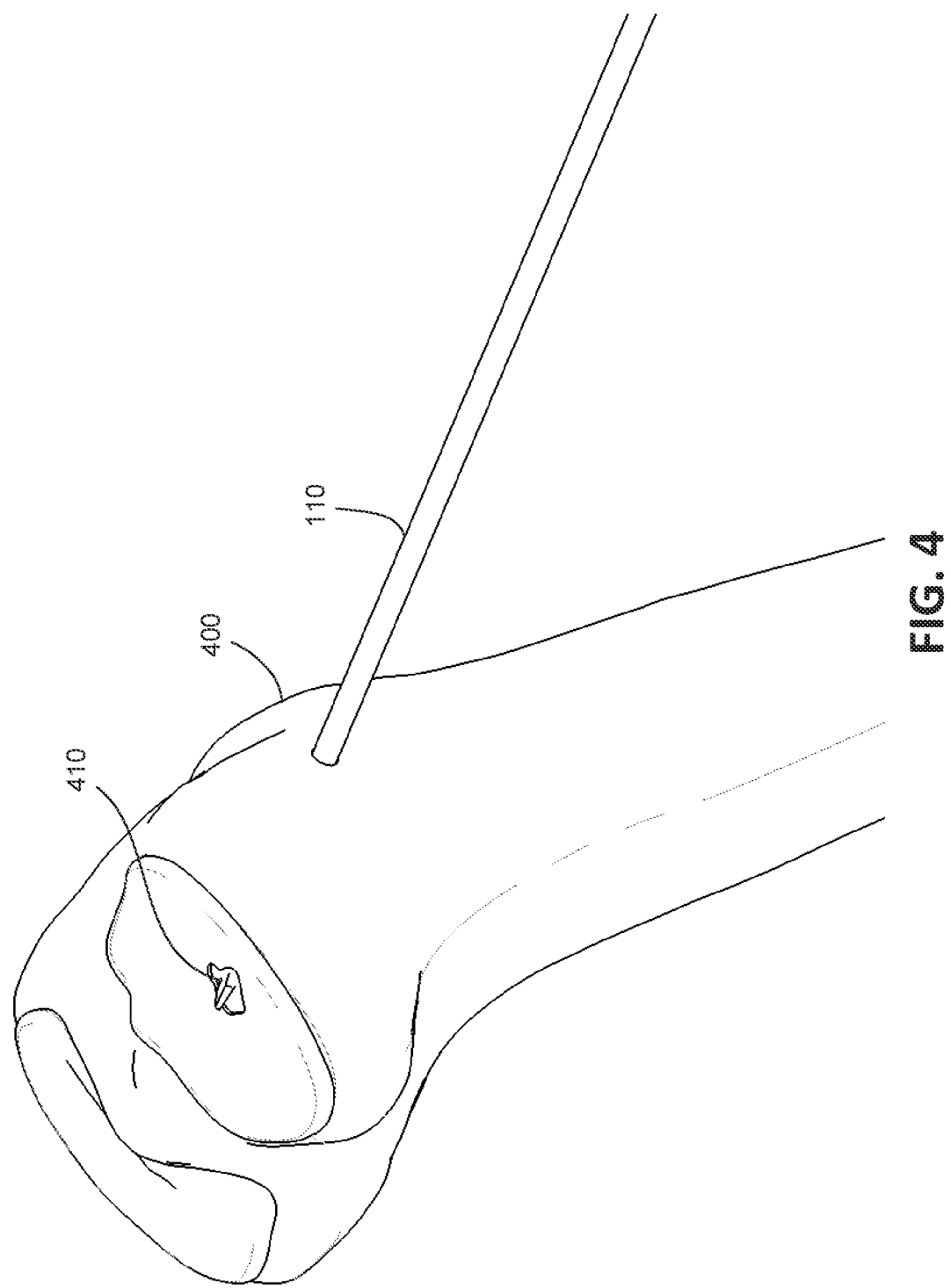

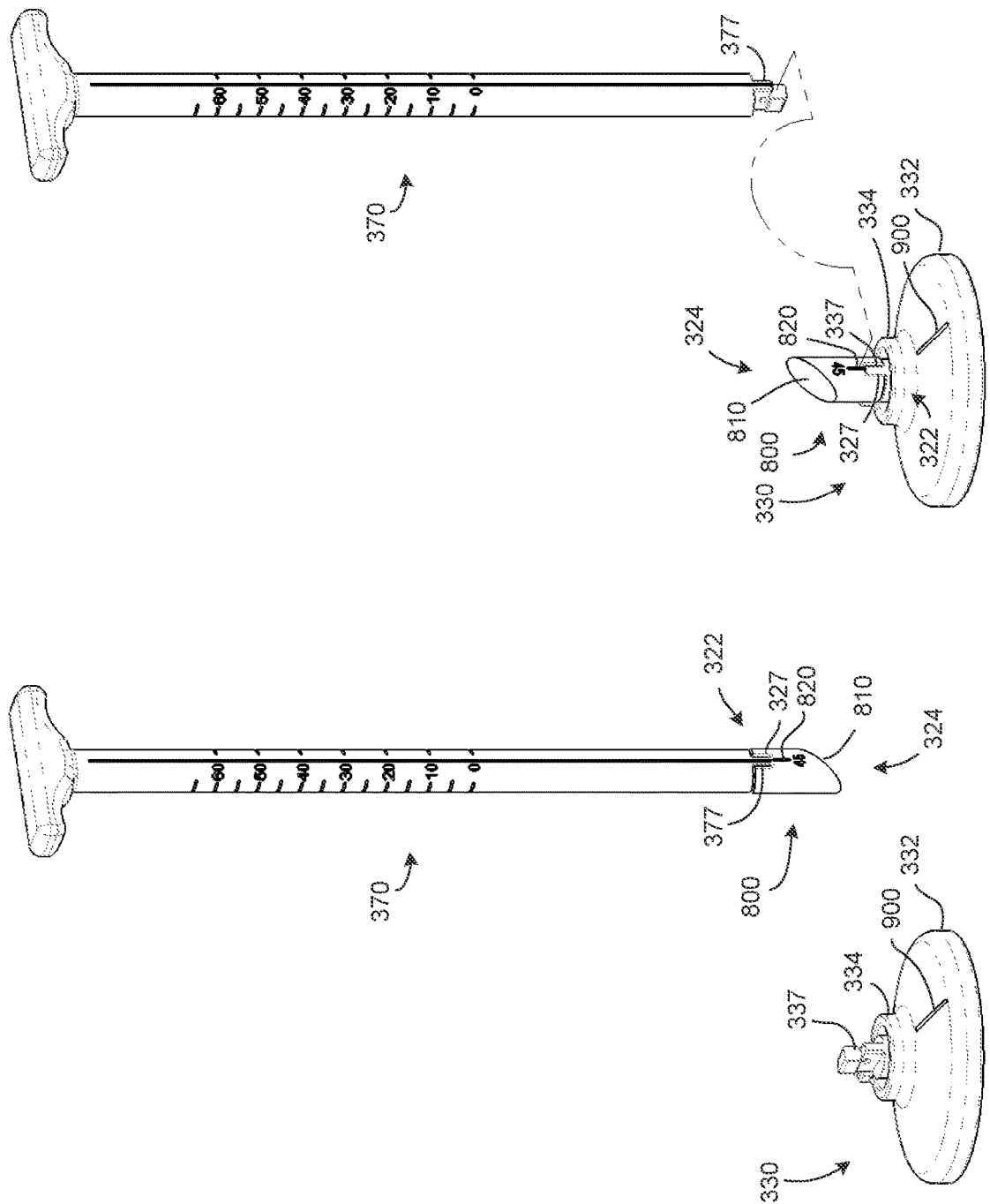

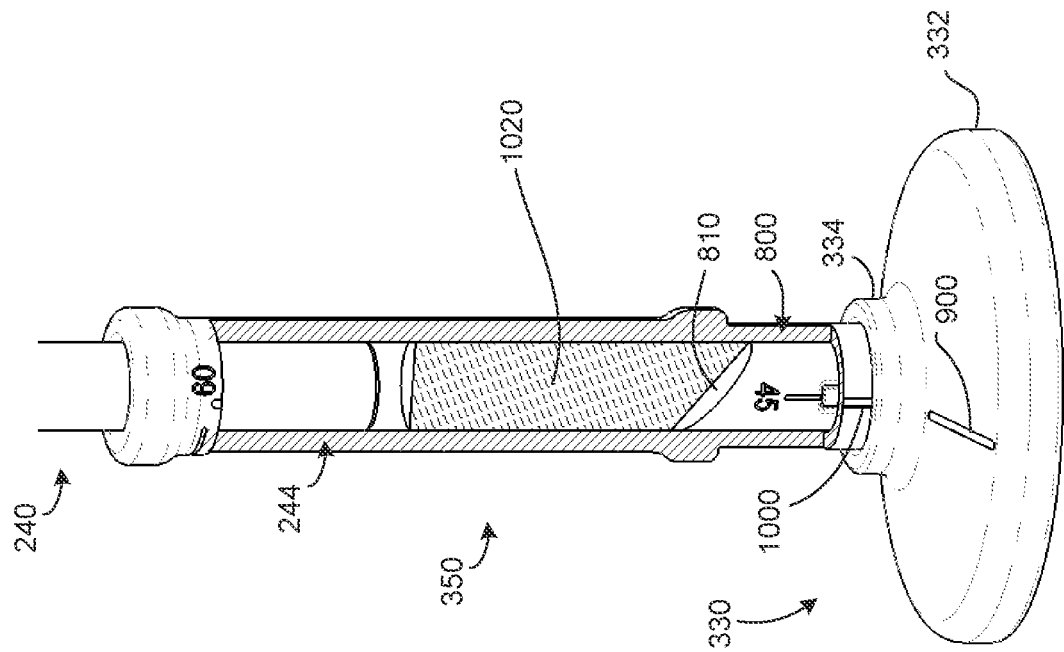
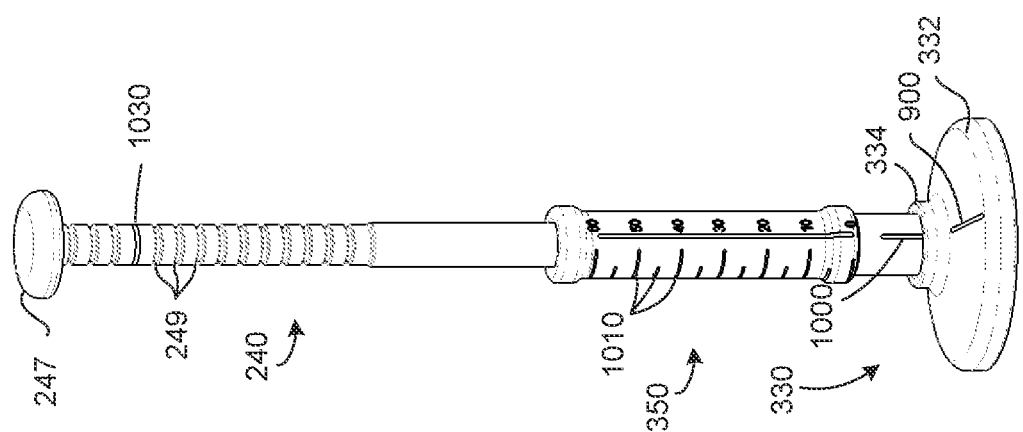
FIG. 10B
FIG. 10A

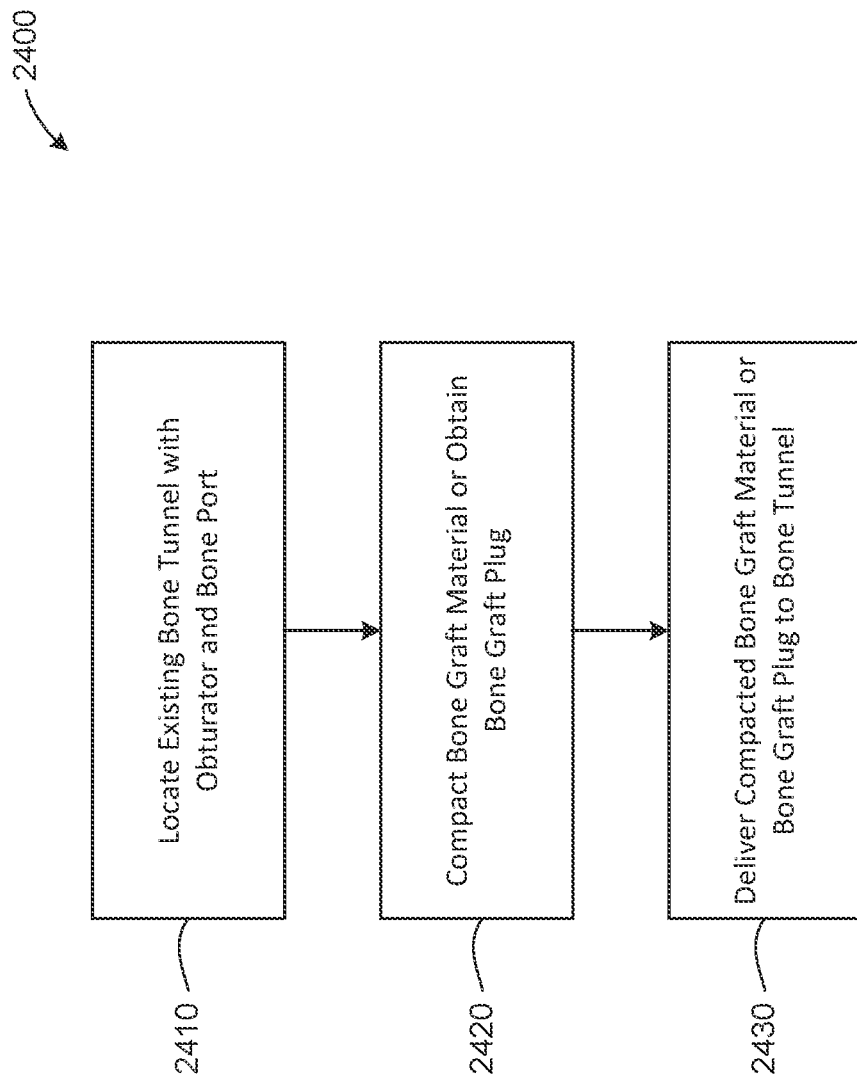

CARTILAGE AND BONE HARVEST AND DELIVERY SYSTEM AND METHODS

TECHNICAL FIELD

The present disclosure relates to systems, methods and devices for bone and cartilage harvesting and delivery. The present disclosure further relates to systems, methods and devices for the repair of osteochondral defects and bone defects.

BACKGROUND

Most surgical repairs of osteochondral lesions (i.e., bone-cartilage lesions) are performed using an antegrade approach, meaning that the approach is from the cartilage side of the bone-cartilage defect. In many cases, because of the location of the lesion, these surgical repairs cannot be performed using an arthroscopic or minimally invasive technique; instead, these surgical repairs require an open procedure, increasing morbidity and the time required to recover from the surgery.

Another limitation of current surgical techniques for osteochondral lesion repair is the use of autograft or allograft osteochondral "plugs," in which the plug is an intact specimen of cartilage with underlying bone taken from a single anatomic site. In the case of autograft osteochondral plugs, there are limitations to the size and number of plugs available in a patient. Furthermore, there is a notable risk of morbidity at the plug harvest site, such as post-operative pain and arthritic changes at the harvest site. In the case of allograft osteochondral plugs, there is a risk of an adverse immunological response as well as a risk of disease transmission.

Using a retrograde approach to surgically repair an osteochondral lesion, where the approach is from the bone side of the cartilage-bone defect, has several advantages over an antegrade approach. One major advantage is that the retrograde approach can be performed arthroscopically. Another advantage is the opportunity to use the bone and cartilage that is removed to obtain access to the lesion as autograft material for the repair. Existing retrograde approaches are technically demanding and rarely used in clinical practice.

There is a need for a simpler, more reproduceable, more reliable surgical technique for a retrograde approach for repairs of osteochondral lesions. Additionally, there is a need for alternative osteochondral graft materials that avoid the risks and complications associated with the use of autograft or allograft osteochondral plugs.

SUMMARY

The various bone and cartilage harvesting and delivery devices, systems, and methods of the present disclosure have been developed in response to the present state of the art, and in particular, in response to the problems and needs in the art that have not yet been fully solved by currently available bone and cartilage harvesting and delivery devices, systems, and methods. In some embodiments, the bone and cartilage harvesting and delivery devices, systems, and methods of the present disclosure may provide improved bone and cartilage harvesting and delivery methods for treating bone, cartilage and osteochondral defects.

According to some embodiments, a system for harvesting tissue material, including bone and cartilage tissue, from a body, may include a rotary cutter defining a rotary cutter longitudinal axis extending between a rotary cutter proximal end and a rotary cutter distal end. The rotary cutter may have a drive shaft configured to receive input torque, and an osteochondral cutter configured to cut tissue and receive the tissue material in response to rotation of the osteochondral cutter under pressure against the tissue. The system may further have a bone port defining a bone port longitudinal axis extending between a bone port proximal end and a bone port distal end. The bone port may have a bone port cannulation sized to closely fit over the osteochondral cutter. At least one of the bone port proximal end and the bone port distal end may be securable to a bone.

The system may further include a plurality of additional rotary cutters, each of which comprises an osteochondral cutter having an outer diameter different from an outer diameter of the rotary cutter, and a plurality of additional bone ports, each of which comprises a bone port cannulation sized to closely fit over the osteochondral cutter of one of the plurality of additional rotary cutters.

The bone port distal end may be configured to be insertable into and retained in the bone.

The system may further include a bone pin comprising a distal end insertable into the bone. The bone port proximal end may have a pin aperture sized to receive the bone pin to secure the bone port proximal end to the bone.

The system may further include a delivery tube defining a delivery tube longitudinal axis extending between a delivery tube proximal end and a delivery tube distal end. The delivery tube distal end may be securable to the bone port proximal end such that the delivery tube longitudinal axis is coaxial with the bone port longitudinal axis.

The system may further include a funnel with a funnel proximal end having a flared shape, and a funnel distal end securable to the bone port and/or the delivery tube.

The system may further include a cap securable to the bone port proximal end. The cap may have a cap port configured to allow instruments to pass through the cap port while maintaining a leak resistant seal.

The system may further include a trial with a trial shaft with a trial shaft proximal end with a handle, and a trial shaft distal end insertable into the bone port cannulation, and a trial tip and configured to approximate a topography of a cartilage or bone surface. The bone port cannulation may be sized to closely fit over the trial tip.

The system may further have a plurality of additional rotary cutters, each of which has an osteochondral cutter having an outer diameter different from an outer diameter of the osteochondral cutter, a plurality of additional trial shafts, each of which has a trial shaft distal end, and a plurality of additional bone ports, each of which has a bone port cannulation sized to closely fit over the osteochondral cutter of one of the plurality of additional rotary cutters and to closely fit over the trial shaft distal end of one of the plurality of additional trial shafts. The system may further include a plurality of additional trial tips, each of which is attachable to the trial shaft distal end.

The plurality of additional trial tips may include at least a first trial tip with a first trial tip distal surface having a first shape, a second trial tip with a second trial tip distal surface having a second shape different from the first shape, and a third trial tip with a third trial tip distal surface having a third shape different from the first shape and the second shape.

The rotary cutter, the plurality of additional rotary cutters, the bone port, and the plurality of additional bone ports may all be configured to be reusable. The trial shaft, the plurality of additional trial shafts, the trial tip, and the plurality of additional trial tips may all be configured to be single-use.

The system may further have a trial with a trial shaft with a trial shaft proximal end having a handle, and a trial shaft distal end insertable into the bone port cannulation, and a trial tip attachable to the trial shaft distal end and configured to approximate a topography of a cartilage surface. The bone port may have orientation markings. At least one of the trial shaft and the trial tip may have a trial timing mark that can be aligned with the orientation markings to orient a tissue graft at a predetermined orientation relative to a graft site in which the tissue graft is to be placed.

According to some embodiments, a system for delivering a tissue graft to a graft site in a bone may have a bone port defining a bone port longitudinal axis extending between a bone port proximal end and a bone port distal end. The bone port may have a bone port cannulation. The system may further include a trial with a trial shaft having a trial shaft proximal end comprising a handle, and a trial shaft distal end insertable into the bone port cannulation, and a trial tip configured to approximate a topography of a cartilage surface. The bone port cannulation may be sized to closely fit over the trial shaft distal end and the trial tip. At least one of the bone port proximal end and the bone port distal end may be securable to the bone.

The bone port distal end may be configured to be insertable into and retained in the bone.

The system may further include a bone pin with a distal end insertable into the bone. The bone port proximal end may have a pin aperture sized to receive the bone pin to secure the bone port proximal end to the bone.

The system may further include a delivery tube defining a delivery tube longitudinal axis extending between a delivery tube proximal end and a delivery tube distal end. The delivery tube distal end may be securable to the bone port proximal end such that the delivery tube longitudinal axis is coaxial with the bone port longitudinal axis.

The system may further include a plurality of additional trial tips including a first trial tip with a first trial tip distal surface oriented at a first angle, a second trial tip with a second trial tip distal surface oriented at a second angle different from the first angle, and a third trial tip with a third trial tip distal surface oriented at a third angle different from the first angle and the second angle.

The bone port may have orientation markings. At least one of the trial shaft and the trial tip may have a trial timing mark that can be aligned with the orientation markings to orient the tissue graft at a predetermined orientation relative to a graft site in which the tissue graft is to be placed.

According to some embodiments, a system for preparing a tissue graft for insertion in a bone may include a delivery tube defining a delivery tube proximal end and a delivery tube distal end, a tamp with a tamp distal end insertable into the delivery tube proximal end, a base securable to the delivery tube distal end, and a plurality of trial tips, each of which is attachable to at least one of the base and the delivery tube distal end. The delivery tube may be sized to fit closely over the tamp distal end and each trial tip of the plurality of trial tips. The plurality of trial tips may include at least a first trial tip with a first trial tip distal surface having a first shape, a second trial tip with a second trial tip distal surface having a second shape different from the first shape, and a third trial tip with a third trial tip distal surface having a third shape different from the first shape and the second shape.

Each of the plurality of trial tips may be attachable to the base, and the base may be attachable to the delivery tube distal end.

The system may further include a bone port defining a bone port longitudinal axis o extending between a bone port proximal end and a bone port distal end. The bone port may have a bone port cannulation sized to closely fit around the tissue graft. At least one of the bone port proximal end and the bone port distal end may be securable to the bone. The delivery tube distal end may be securable to the bone port proximal end.

The bone port may have orientation markings. The delivery tube may have a trial timing mark that can be aligned with the orientation markings to orient the tissue graft at a predetermined orientation relative to a graft site in which the tissue graft is to be placed.

According to some embodiments, a system for harvesting tissue material from a body, preparing a tissue graft, and delivering the tissue graft to a graft site, may include a first rotary cutter defining a rotary cutter longitudinal axis extending between a rotary cutter proximal end and a rotary cutter distal end. The first rotary cutter may have a drive shaft configured to receive input torque, and an osteochondral cutter configured to cut tissue and receive the tissue material in response to rotation of the osteochondral cutter under pressure against the tissue. The system may further include a bone port defining a bone port longitudinal axis extending between a bone port proximal end and a bone port distal end, the bone port comprising a bone port cannulation, a delivery tube defining a delivery tube proximal end and a delivery tube distal end, a base securable to the delivery tube distal end, and a trial. The trial may include a trial shaft with a trial shaft proximal end with a handle, and a trial shaft distal end. The trial may further include a trial tip attachable to the trial shaft distal end, and a plurality of additional trial tips, each of which is attachable to the base and to the trial shaft distal end. At least one of the bone port proximal end and the bone port distal end may be securable to a bone. The bone port cannulation may be sized to closely fit over the trial tip and the osteochondral cutter. The delivery tube may be sized to fit closely over the trial shaft distal end and each trial tip of the plurality of additional trial tips. The plurality of additional trial tips may include at least a first trial tip with a first trial tip distal surface having a first shape, a second trial tip with a second trial tip distal surface having a second shape different from the first shape, and a third trial tip with a third trial tip distal surface having a third shape different from the first shape and the second shape.

According to some embodiments, a method of treating an osteochondral defect may include determining a local cartilage topography or a local subchondral bone topography surrounding a perimeter of an osteochondral defect, wherein the perimeter is circumscribed by a tunnel with a retrograde approach through a bone and through the osteochondral defect, and delivering a stratiform osteochondral graft, including a bone graft material and a tissue graft material, to the perimeter through the tunnel using the retrograde approach such that a surface of the tissue graft material closely matches the local cartilage topography or the local subchondral bone topography.

The bone graft material may be selected from the group consisting of autograft bone, allograft bone, xenograft bone, demineralized bone matrix, bone graft substitutes, extracellular matrix, bone cells, growth factors, blood derivatives, bone marrow aspirate, synthetic bone, and combinations thereof.

The tissue graft material may be selected from the group consisting of autograft cartilage, allograft cartilage, xenograft cartilage, extracellular matrix, tissue scaffolds, cartilage cells, cell sheets, biological glues, growth factors, blood derivatives, bone marrow aspirate, synthetic cartilage, and combinations thereof.

The method may further include, prior to delivering the stratiform osteochondral graft to the perimeter, fabricating the stratiform osteochondral graft by shaping the stratiform osteochondral graft such that, with the stratiform osteochondral graft in the tunnel, the surface is positionable to match the local cartilage topography or the local subchondral bone topography.

Fabricating the stratiform osteochondral graft may further include shaping the bone graft material such that a surface of the bone graft material closely matches the local cartilage topography or the local subchondral bone topography.

Determining the local cartilage topography or the local subchondral bone topography may include inserting a trial into the tunnel, the trial having a distal surface, advancing the trial through the tunnel until the distal surface aligns with the local cartilage topography or the local subchondral bone topography, and confirming that the distal surface is shaped to match the local cartilage topography or the local subchondral bone topography.

Determining the local subchondral bone topography may include inserting a trial into the tunnel, the trial having a distal edge around the distal surface, advancing the trial through the tunnel until the distal edge of the distal surface aligns with the circumferential edge of the subchondral bone, which is in intimate contact with the circumferential edge of the cartilage, and confirming that the distal edge is shaped to match the local subchondral bone topography.

The trial may have a trial shaft and a trial tip with the distal surface. The method may further include, prior to inserting the trial into the tunnel, selecting the trial tip from a plurality of trial tips that are matable with the trial shaft. The plurality of trial tips may include a plurality of distal surfaces of different shapes and/or orientations. The method may further include mating the trial tip to the trial shaft.

Fabricating the stratiform osteochondral graft may include shaping the tissue graft material to match the distal surface of the trial.

Fabricating the stratiform osteochondral graft may include compressing the bone graft material and/or the tissue graft material in a delivery tube. Delivering the stratiform osteochondral graft to the perimeter may include connecting the delivery tube, containing the stratiform osteochondral graft, to the tunnel, and moving the stratiform osteochondral graft out of the delivery tube and into the tunnel.

The method may further include attaching a bone port proximal end and/or a bone port distal end of a bone port to the bone. Delivering the stratiform osteochondral graft to the perimeter may include inserting the stratiform osteochondral graft through the bone port.

According to some embodiments, a method of fabricating a stratiform osteochondral graft to treat an osteochondral defect may include determining a local cartilage topography or a local subchondral bone topography surrounding a perimeter of the osteochondral defect, shaping a bone graft material, positioning a tissue graft material adjacent to the bone graft material, and causing a surface of the tissue graft material to match the local cartilage topography or the local subchondral bone topography.

The bone graft material may be selected from a group consisting of autograft bone, allograft bone, xenograft bone, demineralized bone matrix, bone graft substitutes, extracellular matrix, bone cells, growth factors, blood derivatives, bone marrow aspirate, synthetic bone, and combinations thereof.

The tissue graft material may be selected from a group consisting of autograft cartilage, allograft cartilage, xenograft cartilage, extracellular matrix, tissue scaffolds, cartilage cells, cell sheets, biological glues, growth factors, blood derivatives, bone marrow aspirate, synthetic cartilage, or combinations thereof.

Shaping the bone graft material may include causing a surface of the bone graft material to match the local cartilage topography or the local subchondral bone topography.

Shaping the bone graft material may include compressing the bone graft material with a first compression force. Causing the surface of the tissue graft material to match the local cartilage topography or the local subchondral bone topography may include compressing the tissue graft material with second compression force. The first compression force may be higher than the second compression force.

Causing the surface of the tissue graft material to match the local cartilage topography or the local subchondral bone topography may include causing a bone graft material surface of the bone graft material to match the local subchondral bone topography, and causing a tissue graft material surface of the tissue graft material to match the local cartilage topography.

According to some embodiments, a method of delivering a stratiform osteochondral graft to a bone tunnel in a bone may include attaching a bone port proximal end and/or a bone port distal end of a bone port to the bone, attaching a delivery tube distal end of a delivery tube to the bone port proximal end, the delivery tube containing a stratiform osteochondral graft, and delivering the stratiform osteochondral graft to the bone tunnel from the delivery tube through the bone port.

The method may further include, after delivering the stratiform osteochondral graft to the bone tunnel, moving the stratiform osteochondral graft through the bone tunnel such that a surface of the stratiform osteochondral graft matches a local cartilage topography or a local subchondral bone topography surrounding an internal opening of the bone tunnel.

The method may further include, prior to delivering the stratiform osteochondral graft to the bone tunnel, fabricating the stratiform osteochondral graft by shaping the stratiform osteochondral graft such that, with the stratiform osteochondral graft in the bone tunnel, the surface is positionable to match the local cartilage topography or the local subchondral bone topography.

The stratiform osteochondral graft may further include of a bone graft material and a tissue graft material.

The bone graft material may be selected from a group consisting of autograft bone, allograft bone, xenograft bone, demineralized bone matrix, bone graft substitutes, extracellular matrix, bone cells, growth factors, blood derivatives, bone marrow aspirate, synthetic bone, and combinations thereof.

The tissue graft material may be selected from a group consisting of autograft cartilage, allograft cartilage, xenograft cartilage, extracellular matrix, tissue scaffolds, cartilage cells, cell sheets, biological glues, growth factors, blood derivatives, bone marrow aspirate, synthetic cartilage, or combinations thereof.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 4 is a perspective view from a lateral viewpoint of a proximal tibia and a guidewire placed into the tibia and into an osteochondral lesion from a retrograde approach.

FIG. 9A is a perspective view showing a base next to an angled trial tip connected to a trial shaft.

FIG. 9B is the view of FIG. 9A showing the transfer of an angled trial tip from a trial shaft to a base.

FIG. 10A is a perspective view showing a delivery tube attached to a base with an assembled angled trial tip positioned in the delivery tube with a tamp inserted into the proximal end.

FIG. 10B is a close-up view of FIG. 10A with the delivery tube cut away to show bone graft material compacted proximally by a trial and distally by the angled trial tip.

FIG. 24 is a flow chart showing a method of treating an existing bone tunnel, according to one embodiment.

Figure 1:
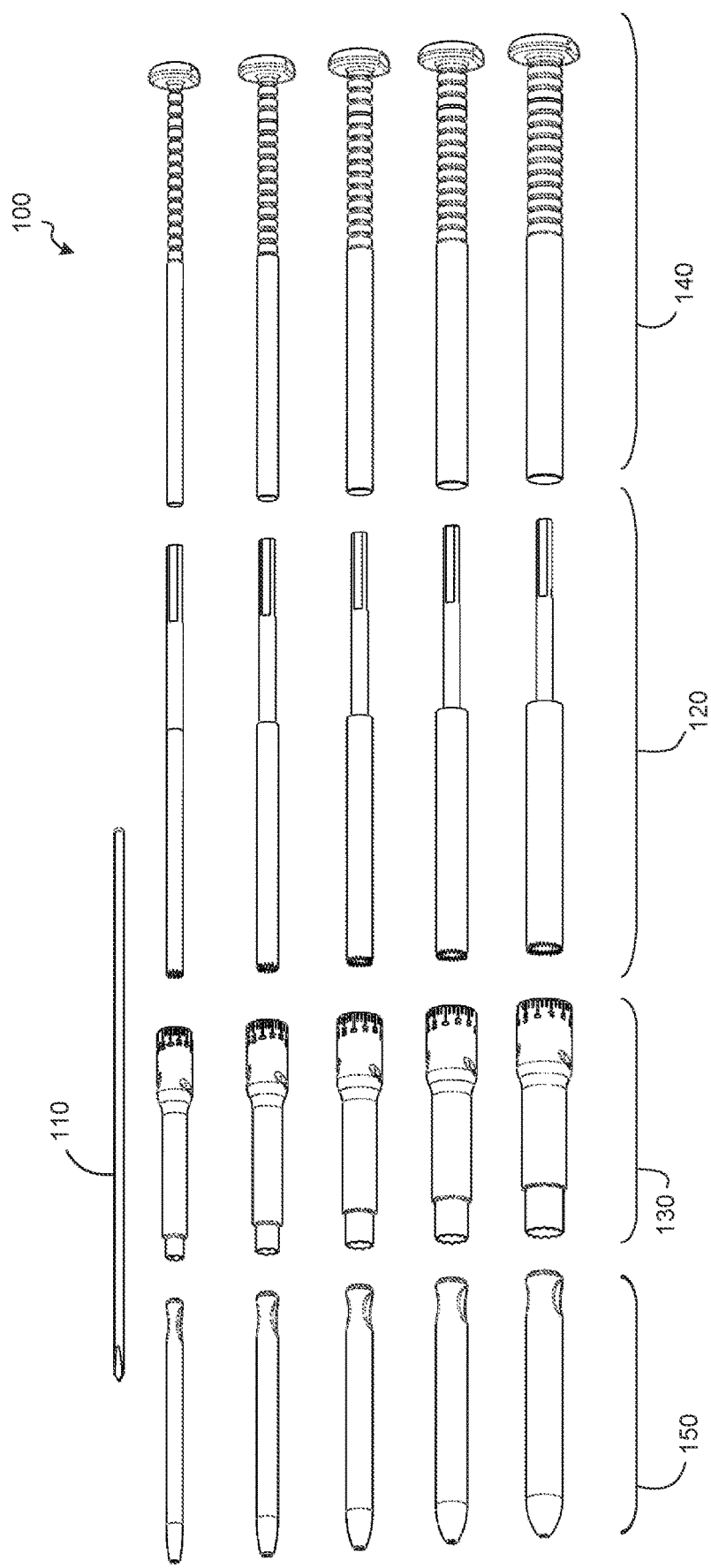
FIG. 1 is a perspective view of a reusable kit of instruments for tissue harvesting and delivery, according to one embodiment.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill in the art can appreciate that the following examples are intended to be exemplary only and that numerous changes, modifications, and alterations can be employed without departing from the scope of the presently disclosed subject matter.

For purposes of interpreting this specification, the following definitions will apply. If any definition set forth below conflicts with any definition incorporated herein by reference, the definition set forth below shall control.

Bone and cartilage, collectively, are referred to as tissue herein. Bone-cartilage defect, osteochondral defect and osteochondral lesion are synonymous, and generally referred to herein as a lesion. Bone marrow edema, focal osteolysis and a bone cyst are generally referred to herein as a bone defect. Proximal means closer to a user, distal means farther away from a user. For example, the handle of a screwdriver is on a proximal end, and the drive tip of a screwdriver is on a distal end.

FIG. 1 is a perspective view of a reusable kit of instruments, or system 100, for tissue harvesting and delivery. The system 100 may include a guidewire 110, a plurality of trephines 120, a plurality of bone ports 130, a plurality of tamps 140, and a plurality of obturators 150. The trephines 120, bone ports 130, tamps 140, and obturators 150 are each shown in 5 sizes, ranging from 6 mm to 14 mm in 2 mm increments, where the size is the size of the tissue tunnel to be formed by the selected subset of the system 100. Other sizes and other increments are possible, for example, ranging from 4 mm to 20 mm in 1 mm increments.

Figure 2:
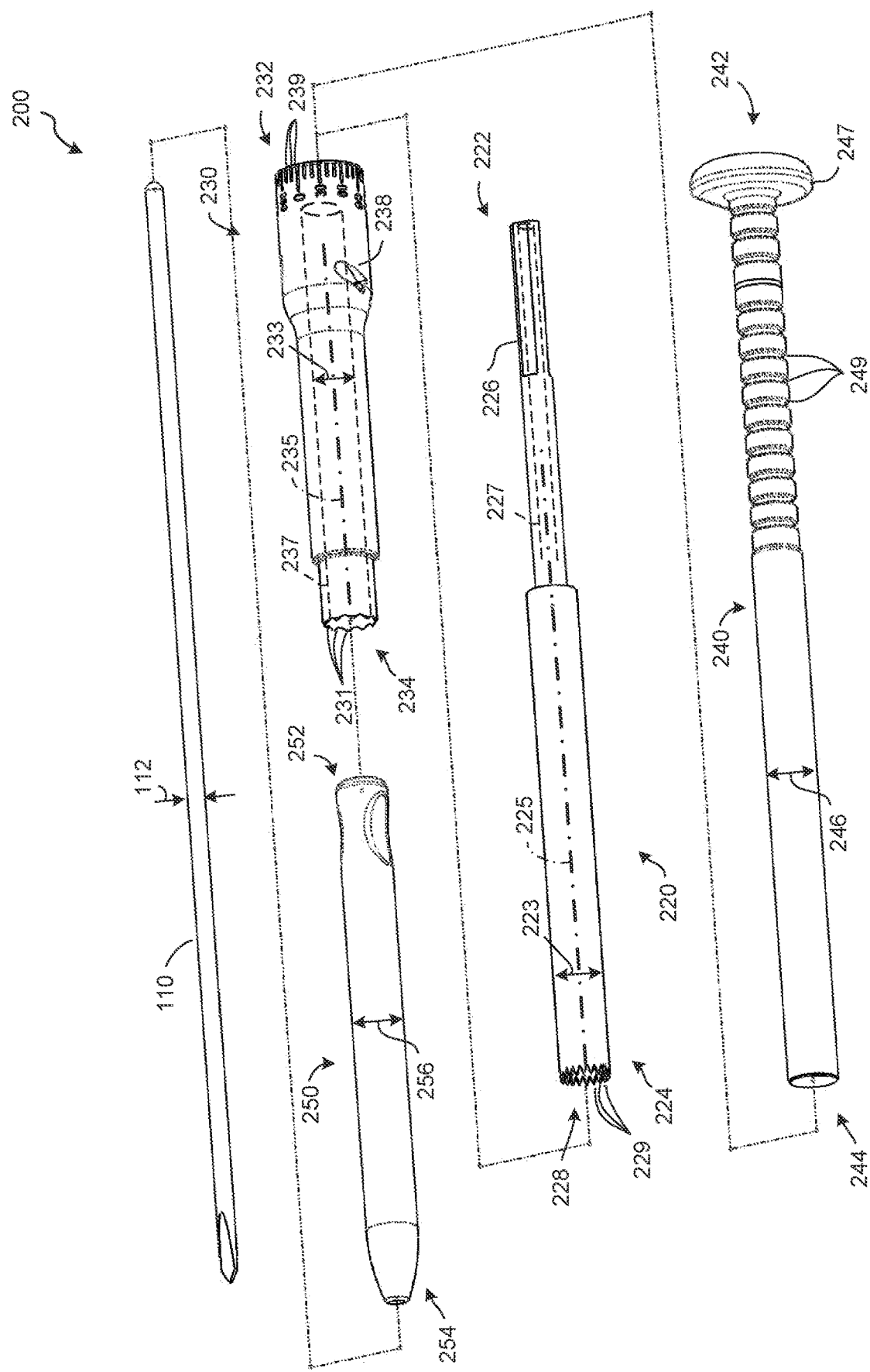
FIG. 2 is an exploded view of a subset of the instruments shown in FIG. 1 for a select tissue tunnel size that have shared interconnection features.

FIG. 2 is an exploded view of a subset 200 of the instruments of the system 100 of FIG. 1 for a select tissue tunnel size that have shared interconnection features. The subset 200 includes the guidewire 110, a trephine 220, a bone port 230, a tamp 240, and an obturator 250. The select tunnel size in this case is 10 mm, or the middle size in the range of sizes in the system 100 of FIG. 1.

The guidewire 110 may be a surgical guide wire of any known type, such as a K-wire or Steinmann Pin. The guidewire 110 may have a guidewire outer diameter 112.

The trephine 220 may have a trephine proximal end 222, a trephine distal end 224, a trephine longitudinal axis 225 extending between the trephine proximal end 222 and the trephine distal end 224, a drive shaft 226 located near the trephine proximal end 222, and a drive shaft cannulation 227 extending along the trephine longitudinal axis 225. The guidewire outer diameter 112 may be sized to closely fit inside the drive shaft cannulation 227, optionally with some clearance so that the trephine 220 can slide along the guidewire 110. Approaching the trephine distal end 224, the trephine 220 may have an osteochondral cutter 228 terminating in a set of teeth 229 configured to cut tissue as the trephine 220 is rotated and pressed against tissue, forming a tunnel. The osteochondral cutter 228 may have a trephine outer diameter 223.

The trephine 220 is just one of many different types of rotary cutters that may be used to cut tissue according to the present disclosure. In alternative embodiments, different rotary cutters, such as drills, reamers, and/or augers, may be used in addition to or in place of the trephine 220. The term "rotary cutter" encompasses all of these alternatives in addition to a trephine.

The bone port 230 may have a bone port proximal end 232, a bone port distal end 234, a bone port longitudinal axis 235 extending between the bone port proximal end 232 and bone port distal end 234, and a bone port cannulation 237. The bone port cannulation 237 may have a bone port inner diameter 233 sized to closely fit over the outer diameter of the osteochondral cutter 228 so that the bone port longitudinal axis 235 and the trephine longitudinal axis 225 are coaxial when the bone port 230 and the trephine 220 are engaged. Further, the bone port 230 may have a pin aperture 238 and a series of orientation markings 239 proximate the bone port proximal end 232. Teeth 231 on the bone port distal end 234 may help anchor the bone port 230 to bone when tapped or drilled into place.

The tamp 240 may have a tamp proximal end 242, tamp distal end 244, and a tamp outer diameter 246. The tamp proximal end 242 may have a handle 247 that is designed to be pressed by hand and/or impacted with a mallet or other instrument to compress graft material at the tamp distal end 244. A series of depth markings, such as circumferential grooves 249, may be arranged along the length of the proximal portion of the tamp 240, and may help the user gauge the motion travelled by the tamp 240 in the course of compacting tissue material, and thence, the degree of compaction applied by the tamp 240 to the tissue material. Additionally, the tamp distal end 244 may be used to move graft material from one position to another.

The obturator 250 may have an obturator proximal end 252, an obturator distal end 254, and an obturator outer diameter 256, which may be substantially equal to the trephine outer diameter 223, the bone port inner diameter 233, and the tamp outer diameter 246. The obturator distal end 254 may be tapered to facilitate insertion of the obturator 250 into an opening tissue, such as a pre-existing bone tunnel, in order to widen and/or prepare the opening for further steps.

The guidewire 110, the trephine 220, the bone port 230, the tamp 240, and/or the obturator 250 may be designed for reuse. Thus, these components may be formed of durable and readily sterilizable, and re-sterilizable, materials, such as stainless steel, or any other material known for use in the manufacture of surgical instruments. In alternative embodiments, one or more of these components may be designed for single use, and may thus be formed of less durable materials, such as plastics, if desired. In the present embodiment, the components of the system 100 may be designed for use with a system 300 of single use components. The system 100 and the system 300 may combine to define a system with reusable components (from the system 100) and disposable components (from the system 300). In some embodiments, the components of the system 100 may be sterilized and provided in a reusable assembly such as a re-sterilizable instrument tray. The components of the system 300 may also be sterilized, but may be provided in disposable, single-use packaging, such as one or more sealed plastic packages. The components of the system 300 may be formed of less expensive less durable materials, such as plastic materials, if desired. Alternatively, some or all of the components of the system 300 may be formed of durable re-sterilizable materials and added to the reusable instrument tray and/or provided separately.

Figure 3:
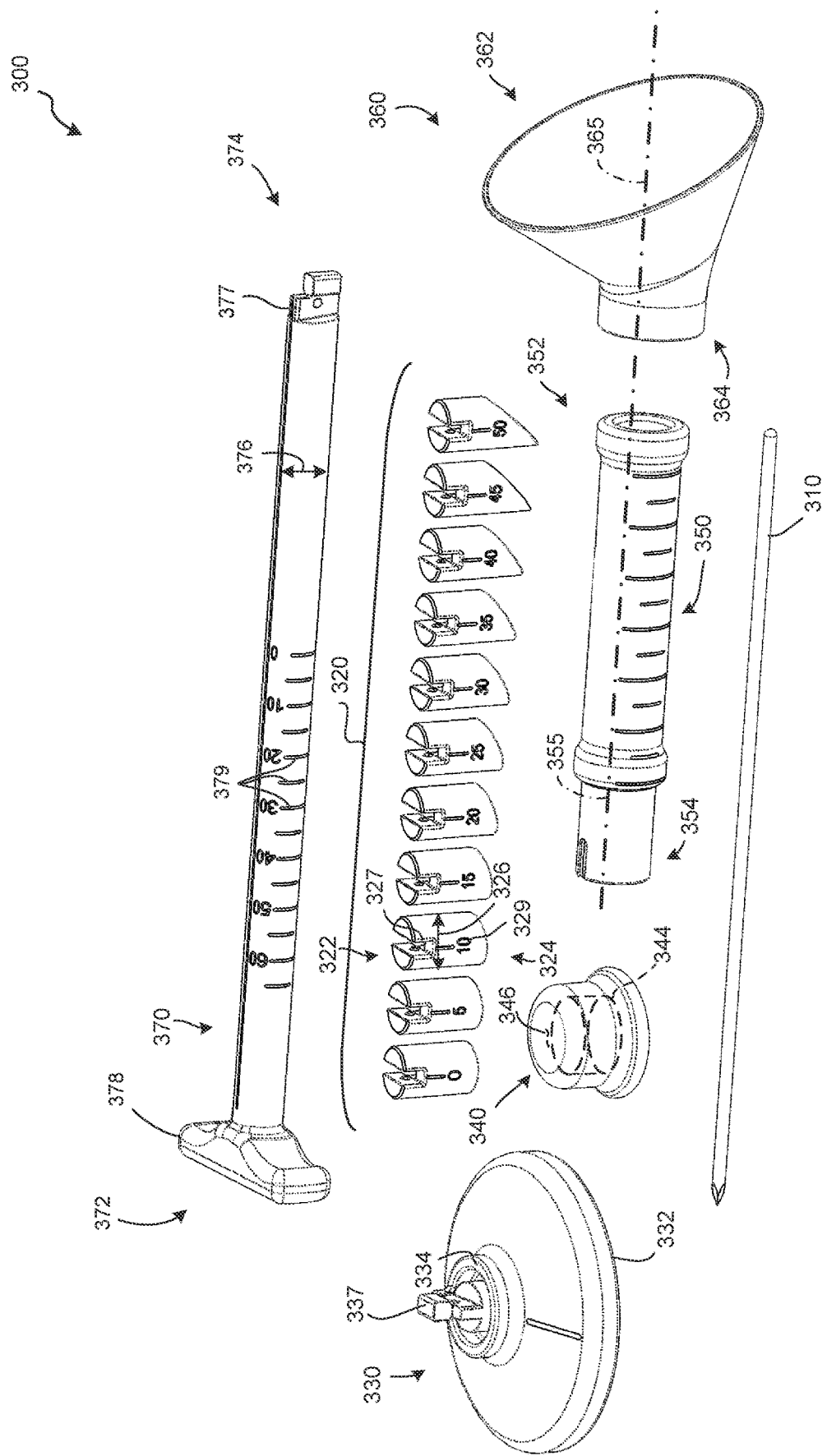
FIG. 3 is a perspective view of a single use kit of instruments that complement the subset of instruments shown in FIG. 1 to facilitate a surgical procedure for a select tissue tunnel size.

FIG. 3 is a perspective view of the system 300, which may be a single use kit of instruments that complements the system 100 shown in FIG. 1 to facilitate a surgical procedure for the select tissue tunnel size of 10 mm. Separate systems may be provided for each size tissue tunnel that is desired for treatment. For example, in addition to the system 300, additional systems (not shown) may be provided along with the system 100 to facilitate treatment using 6 mm, 8 mm, 12 mm, and 14 mm tissue tunnels. The system 300 may include a fixation pin 310, a plurality of trial tips 320, a base 330, a cap 340, a delivery tube 350, a funnel 360, and a trial shaft 370.

Like the guidewire 110, the fixation pin 310 may be any type of bone pin known in the art. For example, the fixation pin 310 may be a k-wire or the like. The fixation pin 310 may be sized to slide into the pin aperture 238 of the bone port 230, and may fit sufficiently tightly within the pin aperture 238 such that the bone port 230 is maintained at a constant relative orientation by engagement of the pin aperture 238 with the guidewire 310.

Each of the trial tips 320 may have a trial tip proximal end 322, a trial tip distal end 324, and a trial tip outer diameter 326. Each of the trial tips 320 may further have an attachment feature, such as a slot 327, that facilitates attachment to the base 330 and/or the trial shaft 370. Thus, each of the trial tips 320 may be interchangeably attachable to the same male attachment feature.

Each trial tip distal end 324 may be planar, but the orientation of the trial tip distal end 324 may vary among the trial tips 320. The orientation of the trial tip distal end 324 may range, among the trial tips, 320, from 0° to 50°, measured as the offset from a plane perpendicular to the axis extending from the trial tip proximal end 322 to the trial tip distal end 324. Each of the trial tips 320 may have an angle indicator 329 that indicates the orientation of the trial tip distal end 324.

In alternative embodiments, different increments may be used; such increments may be greater than or smaller than 5° (for example, 1°, 2°, 3°, 4°, 5°, 6°, 7°, 8°, 9°, 10°, 12.5°, 15°, 20°, 22.5°, or)25°. Further, the orientation of the trial tip distal end 324 need not have a maximum of 50°; a smaller or greater maximum orientation may be used (for example, 20°, 25°, 30°, 35°, 40°, 45°, 50°, 55°, 60°, 65°, 70°, 75°, or)80°. In some embodiments, where it is desired to approach an osteochondral defect from an orientation nearly parallel to the cartilage surface, the maximum orientation may approach 90°.

Figure 8A:
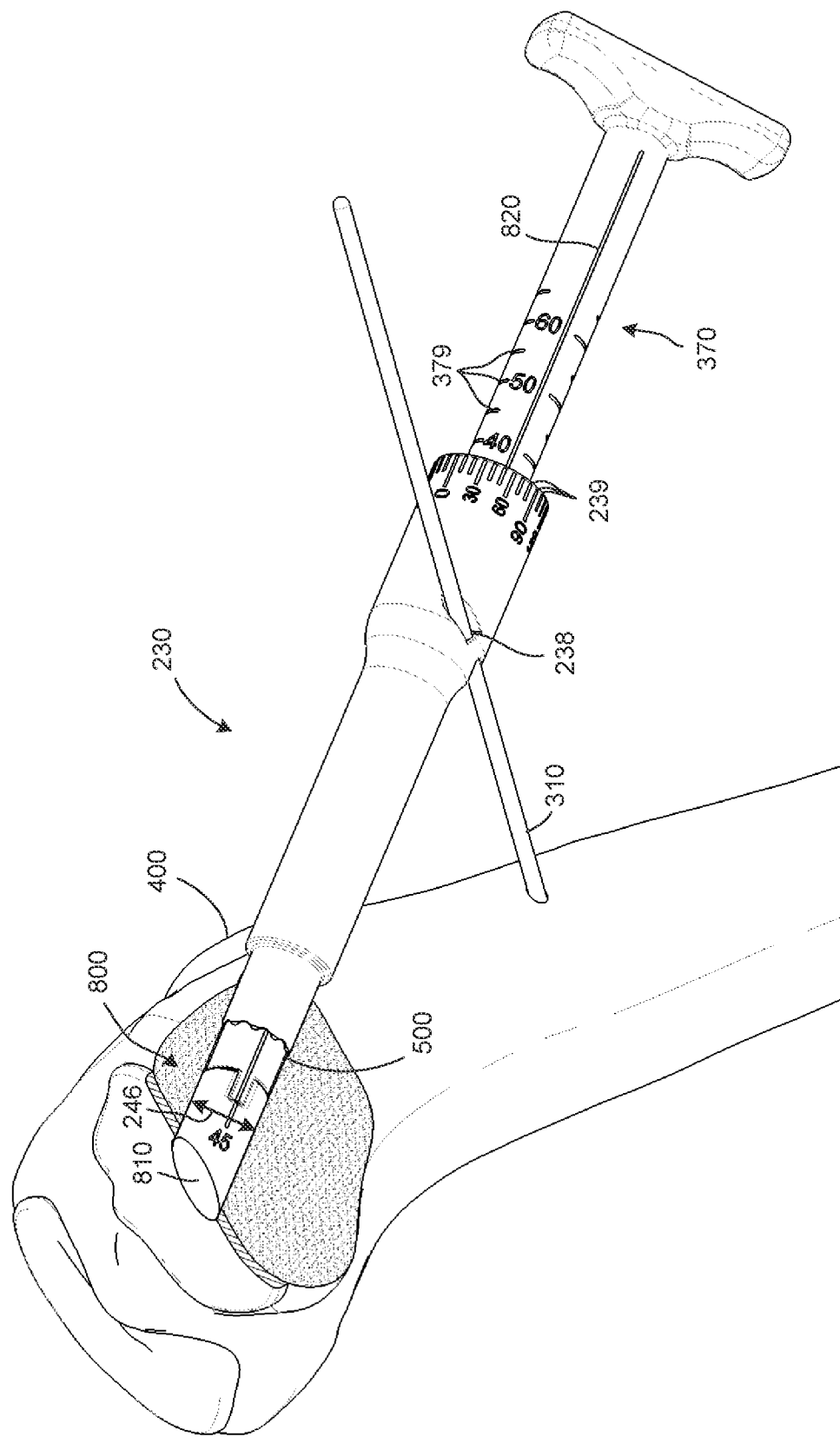
FIG. 8A is a perspective view from a lateral viewpoint of the proximal tibia shown in partial cross section and a trial shaft with an attached angled trial tip placed through a bone portal and with the trial tip distal end positioned to match the surface topography of the surrounding cartilage.
Figure 8B:
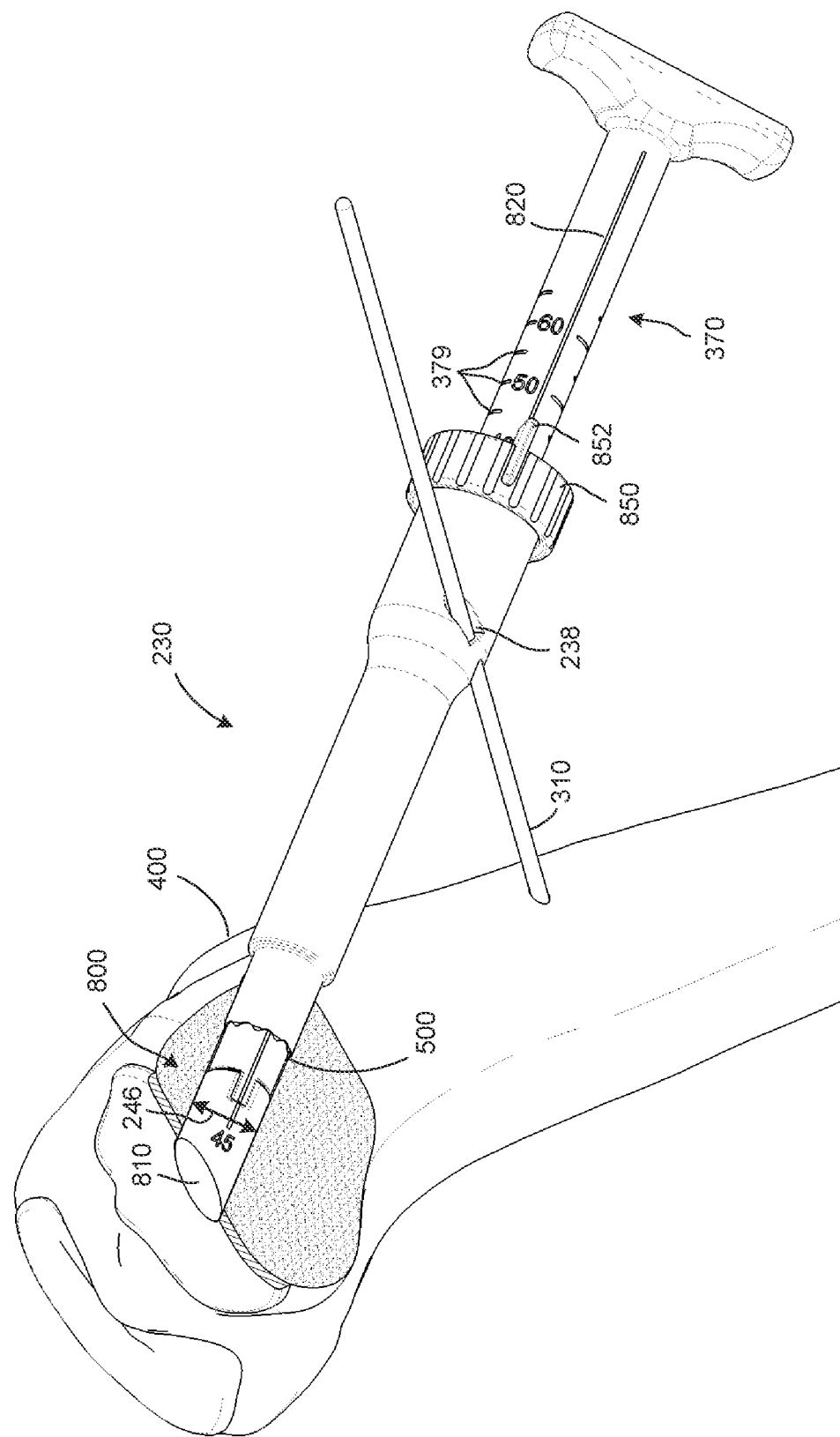
FIG. 8B is a perspective view from a lateral viewpoint of the proximal tibia shown in partial cross section and a trial shaft with an attached angled trial tip placed through a bone portal and with the trial tip distal end positioned to match the surface topography of the surrounding cartilage.
Figure 11:
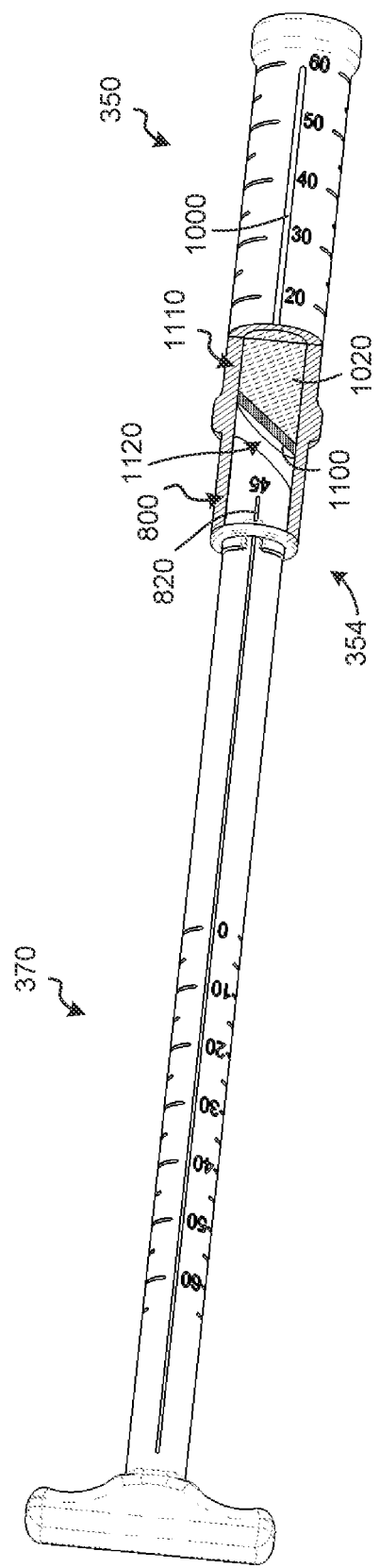
FIG. 11 is a perspective view in partial cross-section showing cartilage graft material compacted into the distal end of the delivery tube distally by an angled trial tip to fabricate a stratiform osteochondral graft.

In alternative embodiments, the trial tip distal end 324 of the trial tips 320 may have any range of unique shapes, including concave, convex, or even more complex shapes. Additionally or alternatively, the trial tip distal end 324 of each of the trial tips 320 may be shaped to match a specific cartilage topography for a specific osteochondral defect for a specific patient. For trial tip distal ends that are not planar, two trial tips with complementary shapes (not shown) may be used for a specific osteochondral defect. The first trial tip may directly correspond to a cartilage surface when it is used as a trial as shown in FIG. 8A and FIG. 8B, and the second trial tip may correspond to the negative (i.e., a Boolean subtraction) of the cartilage surface when it is used to compact bone graft material and cartilage graft material as shown in FIG. 10B and FIG. 11.

The base 330 may have a body 332, a plateau 334, and an attachment feature configured to mate with the slot 327 of the trial tips 320, such as a slider 337. The body 332 may have an enlarged shape that can be readily grasped by a user and/or placed on a flat surface during use. The plateau 334 may have a width similar in size to that of the delivery tube 350. The plateau 334 and/or the slider 337 may optionally be incorporated into an insert, separate from the body 332, that can be assembled with the body 332 (for example, via insertion of the insert into a hole in the body 332) to provide the assembled configuration shown in FIG. 3.

The cap 340 may be sized to fit over the bone port proximal end 232 and/or the delivery tube proximal end 352. Thus, the cap 340 may have a bore 344 with an interior diameter (not shown) that is close to the outer diameter of the bone port proximal end 232 and the delivery tube proximal end 352. The cap 340 may further have a cap port 346 that provides a leak resistant seal. The cap port 346 may be flexible and self-closing, so that instruments can be passed through the cap port 346 and still maintain a leak resistant seal. The cap 340 may be formed of a resilient, flexible material, such as rubber, to help provide a seal between the cap 340 and the bone port proximal end 232 and/or the delivery tube proximal end 352, and the seal provided by the cap port 346.

The delivery tube 350 may have a delivery tube proximal end 352, a delivery tube distal end 354, and a delivery tube longitudinal axis 355 extending between the delivery tube proximal end 352 and delivery tube distal end 354. The delivery tube distal end 354 may be sized to closely fit into the bone port proximal end 232 so that the delivery tube longitudinal axis 355 and the bone port longitudinal axis 235 are coaxial when the delivery tube 350 and the bone port 230 are coupled together.

The funnel 360 may have a funnel proximal end 362, a funnel distal end 364, a funnel longitudinal axis 365 extending between the funnel proximal end 362 and funnel distal end 364. The funnel distal end 364 may be sized to closely fit into the bone port proximal end 232 and/or the delivery tube proximal end 352 and/or delivery tube distal end 354, so that the funnel longitudinal axis 365 is coaxial with the bone port longitudinal axis 235 or the delivery tube longitudinal axis 355, respectively. The funnel proximal end 362 may have a flared shape configured to facilitate insertion of graft material and instruments into the funnel 360, and thence into the bone port 230 and/or delivery tube 350.

The trial shaft 370 may have a trial shaft proximal end 372, a trial shaft distal end 374, and a trial shaft outer diameter 376, which may be substantially equal to the trephine outer diameter 223, the bone port inner diameter 233, and the tamp outer diameter 246. The trial shaft distal end 374 may have an attachment feature, such as a slider 377, that is designed to mate with the slot 327 of each of the trial tips 320. The slider 377 may have an enlarged tip and the slot 327 may have a complementary shape so that, when coupled to each other, each of the trial tips 320 cannot be pulled distally away from the trial shaft 370. The trial shaft 370 may further have a handle 378 at the trial shaft proximal end 372, and a series of depth markings 379 between the trial shaft proximal end 372 and the trial shaft distal end 374.

The assembled trial shaft 370 and one of the trial tips 320 are referred to as a trial, which may have an outer diameter substantially equal to the tamp outer diameter 246. To accommodate the select tunnel size of 10 mm, the trephine outer diameter 223 of the osteochondral cutter 228, the inner diameter of the bone port cannulation 237, the tamp outer diameter 246, and the trephine outer diameter 223 may all be nominally 10 mm in size. Those of skill in the art will recognize that some variation from the nominal size may be desirable; for example, the inner diameter of the bone port cannulation 237 may be slightly larger than the trephine outer diameter 223, the trial tip outer diameter 326, and the trial shaft outer diameter 376 so that the trephine 220, each of the trial tips 320, and/or the trial shaft 370 may be inserted and relatively freely slide into the bone port cannulation 237 of the bone port 230.

While the mating connections between bone port 230, delivery tube 350, funnel 360, and cap 340 are shown with specific male and female arrangements, in alternative embodiments (not shown), the connections can be easily reversed and still preserve the coaxial relationship between respective longitudinal axes required to ensure proper function. Further, many different mating and non-mating connections may be used, including but not limited to clips, claps, mechanical fasteners, bayonet fittings, and/or the like.

The system 100 and/or the system 300 may be used to help repair osteochondral defects in bone. In some embodiments, this may be accomplished by (1) harvesting tissue, (2) preparing the harvested tissue, and (3) placing the prepared tissue at the defect site. Notably, this approach assumes that the tissue is natural (i.e., autograft, allograft, or even xenograft). However, the system 100 and/or the system 300 may also be used with synthetic graft or bone graft substitutes; in such cases, (1) and/or (2) above may not be needed.

In some embodiments, the process of harvesting the tissue may be formed as part of the process of removing the osteochondral defect and/or preparing the defect site for repair. Healthy tissue at or around the repair site may be removed, prepared, and inserted back into the repair site, optionally with additional natural or synthetic tissue. FIGS. 4 through 8 illustrate the process of harvesting tissue and preparing a defect site for repair (i.e., step (1) in the preceding paragraph) according to one embodiment.

FIG. 4 is a perspective view from a lateral viewpoint of a proximal tibia 400 with the guidewire 110 placed into the proximal tibia 400 and into the central aspect of an osteochondral lesion 410 from a retrograde approach (i.e., through the tissue beneath the osteochondral lesion 410). The placement of the guidewire 110 into the bone and cartilage can be accomplished using a powered pin driver (not shown), and the guidewire 110 can be placed manually or using a targeting drill guide (not shown) known in the art. Fluoroscopy and/or other medical imaging may be used to guide placement of the guidewire 110. In some embodiments, direction visualization (for example, via arthroscopic cameras inserted into the knee joint) may be used to guide and/or confirm placement of the guidewire 110.

The proximal tibia 400 is used in the figures is for illustrative purposes. The systems and methods of the present disclosure may be used to treat any bone and/or cartilage location in the body. Cartilage is found in all the articular joints of the body. In the example of FIG. 4, the osteochondral lesion 410 is located in the knee joint. Other articular joints in the body that may be treated with the systems and methods presented herein include, but are not limited to: a metatarsal-phalangeal joint, a metatarsal-tarsal joint, a tarsal-tarsal joint, a subtalar joint, a calcaneal-tarsal joint, an ankle joint, a hip joint, a metacarpal-phalangeal joint, a metacarpal-carpal joint, a carpal-carpal joint, a wrist joint, an elbow joint, a shoulder joint, and spine facet joint.

Figure 5A:
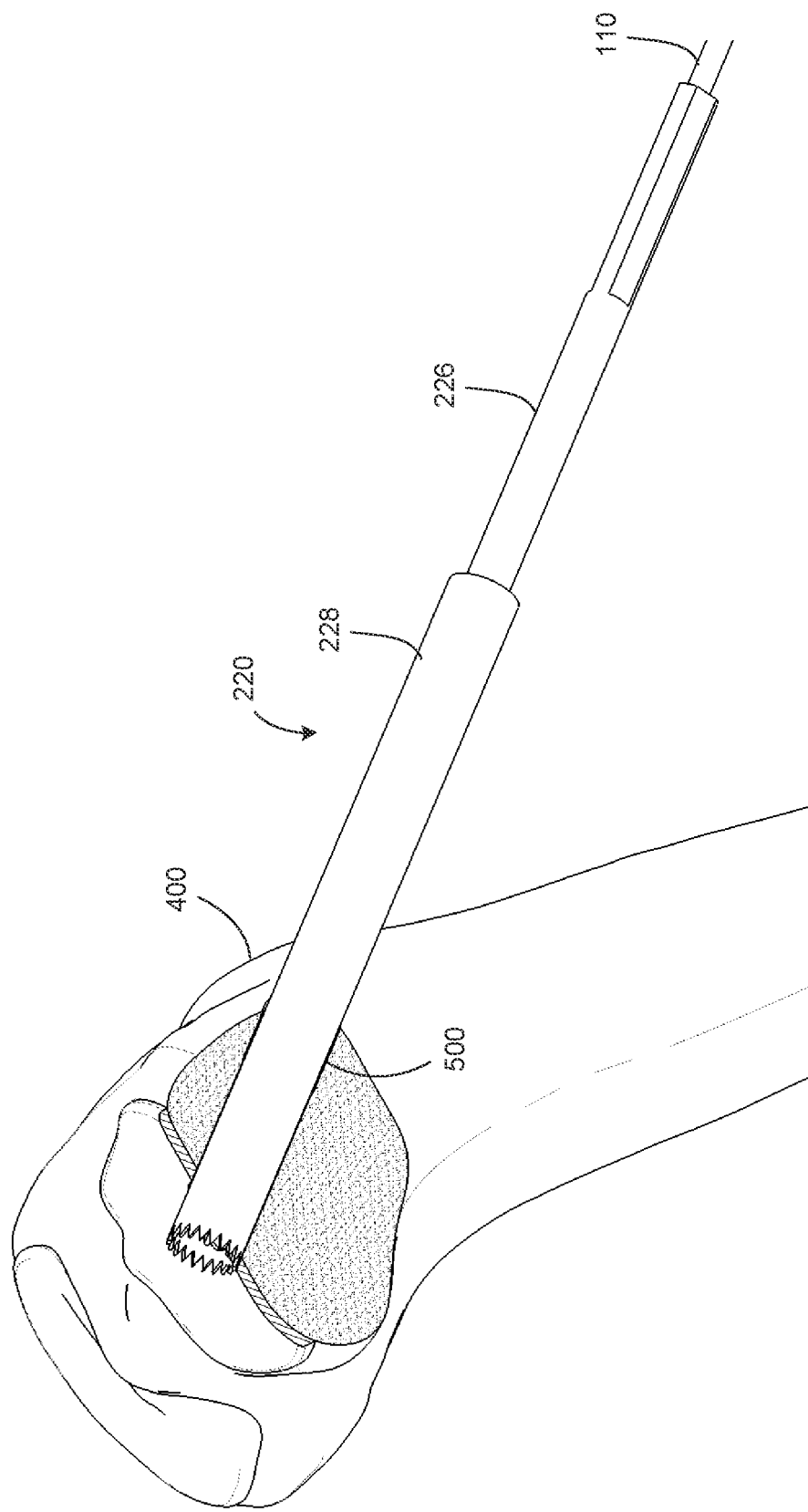
FIG. 5A is a perspective view from a lateral viewpoint of the proximal tibia shown in partial cross section and a trephine placed over the guidewire and into the proximal tibia and through the cartilage from a retrograde approach.

FIG. 5A is a perspective view from a lateral viewpoint of the proximal tibia 400 shown in partial cross section and the trephine 220 placed and slid over the guidewire 110 and into the proximal tibia 400 and through the osteochondral lesion 410 from a retrograde approach, forming a tissue tunnel 500 underneath the repair site. The drive shaft cannulation 227 may fit closely over the guidewire 110 such that the trephine 220 tracks precisely to the osteochondral lesion 410. In an alternative embodiment, a cannulated drill or other cannulated cutter known in the art (not shown) may be used in place of or in addition to the trephine 220 to form the tissue tunnel 500. The tissue tunnel 500 may extend sufficiently far to include the osteochondral lesion 410. In this application, the term "tissue tunnel" is intended to cover tunnels through various types of tissue, including but not limited to tunnels through bone, cartilage, and combinations of bone and cartilage.

In this example, the tissue tunnel 500 may be approximately 10 mm in size because the trephine outer diameter 223 of the osteochondral cutter 228 may be about 10 mm. Any of the trephines 120 of FIG. 1 may be used to provide a tissue tunnel of the appropriate size for a particular joint and/or a particular osteochondral defect.

Figure 5B:
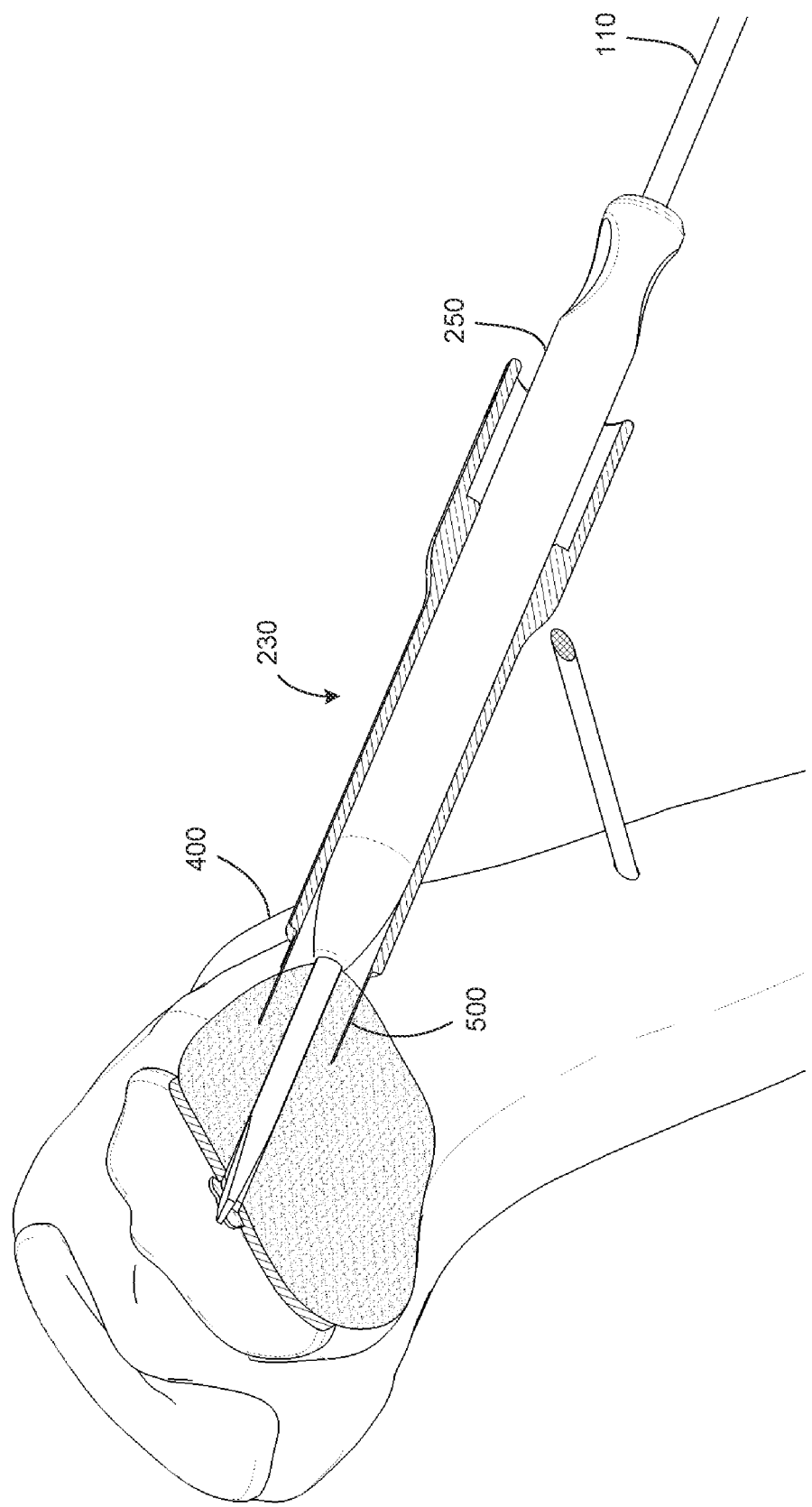
FIG. 5B is a perspective view from a lateral viewpoint of the proximal tibia shown in partial cross section and an obturator placed over the guidewire and a bone port placed over the obturator and into the proximal tibia.

FIG. 5B is a perspective view from a lateral viewpoint of the proximal tibia 400 shown in partial cross section and an obturator 250 placed over the guidewire 110 and a bone port 230 placed over the obturator 250 and into the proximal tibia 400. The obturator 250 may be used to facilitate placement of the bone port 230 such that the bone port cannulation 237 is coaxial with the tissue tunnel 500 (not shown).

Figure 6:
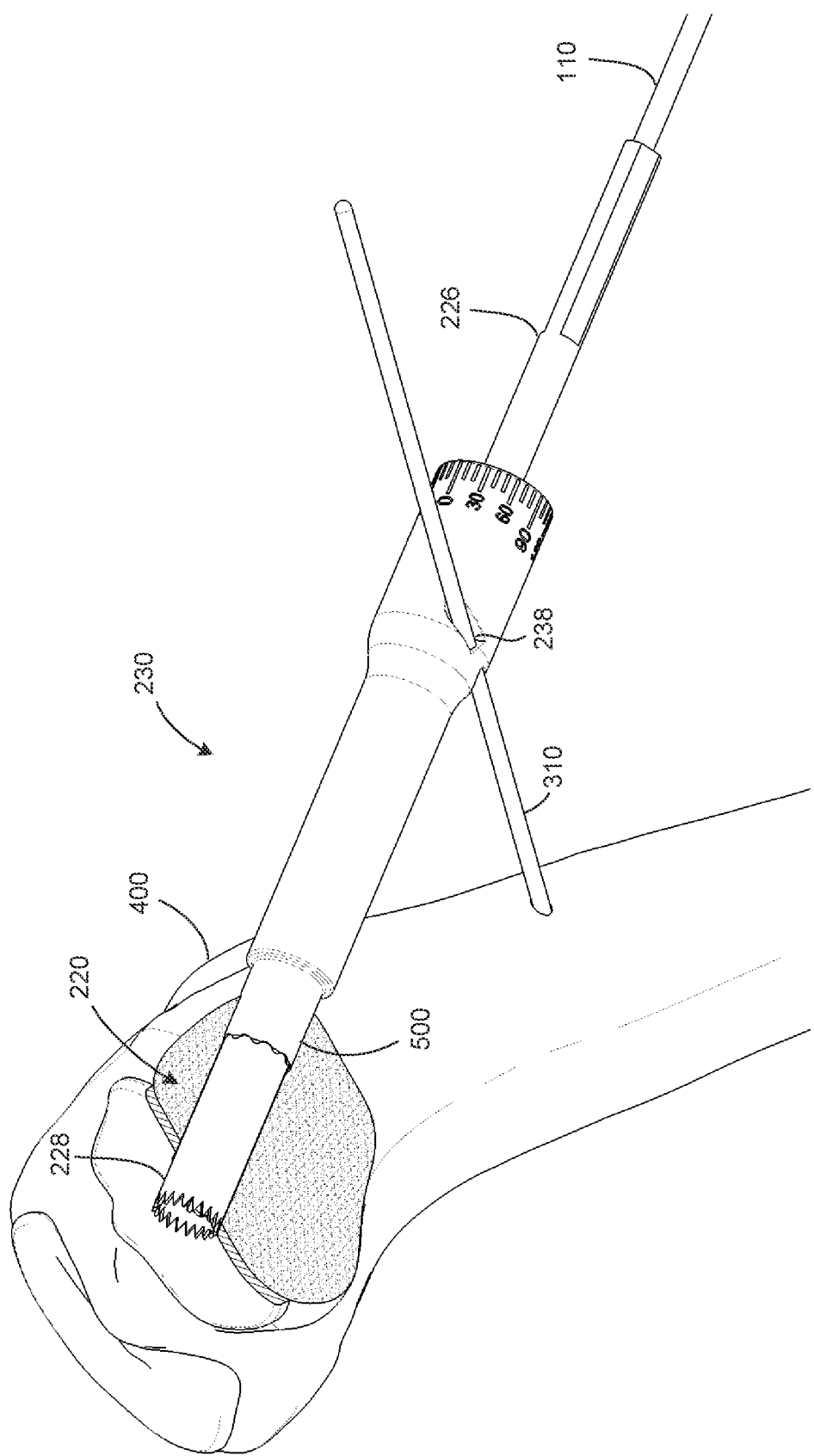
FIG. 6 is a perspective view from a lateral viewpoint of the proximal tibia shown in u partial cross section and a trephine inside of a bone port, and the bone port secured to the tibia.

FIG. 6 is the view of FIG. 5A with the bone port 230 placed and slid over the trephine 220 and secured to the proximal tibia 400. FIG. 6 is also the view of FIG. 5B with bone port 230 used to guide the trephine 220 into the formation of tissue tunnel 500. The bone port inner diameter 233 may closely fit over the trephine outer diameter 223 to ensure that the bone port longitudinal axis 235 and the trephine longitudinal axis 225 are coaxial, irrespective of which is placed first. The teeth 231 on the bone port distal end 234 may be serrated and may allow the bone port distal end 234 to be inserted along the bone port longitudinal axis 235 into the bone, thereby securing the bone port 230 to the bone. Alternatively, or in combination with securing of the bone port distal end 234 to the bone, the bone port 230 can be secured to bone adjacent to the bone port proximal end 232. For example, the pin aperture 238 may receive the fixation pin 310 to secure the bone port 230 to the bone.

Notably, the bone port 230 need not necessarily be used to dilate or retract tissue; rather, these steps may be performed with other instruments, such as the obturator 250, prior to application of the trephine 220. The trephine 220 may guide placement of the bone port 230 as the bone port 230 may be slid into position over the trephine 220, or the bone port 230 may guide placement of the trephine 220. Formation of the tissue tunnel 500 with the trephine 220 prior to attachment of the bone port 230 may facilitate and/or enable the bone port 230 to be used for other functions besides guiding the trephine 220. For example, the bone port 230 may maintain retraction of the surrounding soft tissue such as muscle, fat and skin (not shown). This may be advantageous for subsequent operative steps, such as visualizing the interior of the tissue tunnel 500 with an endoscope (not shown), removing additional tissue from the interior of the tissue tunnel 500, accessing an intra-articular space, and/or delivering bone graft materials and/or cartilage graft materials to the repair site through the tissue tunnel 500.

Figure 7:
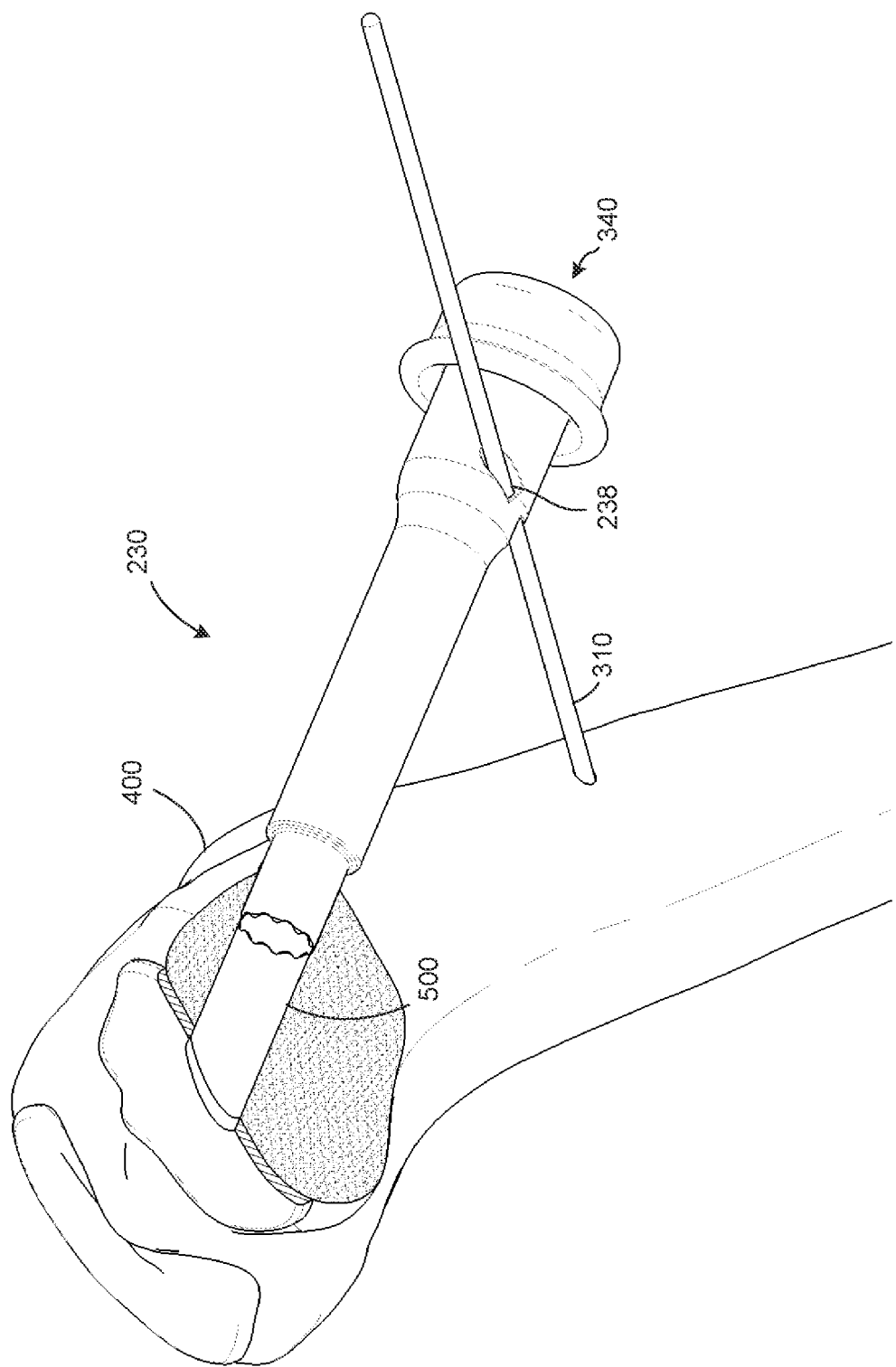
FIG. 7 is the view of FIG. 6 with the trephine removed and a cap attached to a bone port.

FIG. 7 is the view of FIG. 6 with the trephine 220 removed. With the trephine 220 removed, a user may attach the cap 340 to the bone port proximal end 232 to form a leak resistant seal to facilitate the performance of an arthroscopic procedure in the knee joint space. The cap port 346 may provide another leak resistant seal when instruments are passed through the cap port 346. For example, the user can insert an endoscope (not shown) through the cap port 346 and into the tissue tunnel 500 to allow for direct visualization of the cartilage layer and underlying bone to ensure that all the damaged/diseased cartilage and/or bone associated with the osteochondral lesion 410 have been removed. If damaged/diseased cartilage and/or bone remain, then the user can pass a curette or other cutting instrument (not shown) to excavate the remaining damaged/diseased tissue.

Loose tissue may be removed from the tissue tunnel 500. Much of the loose tissue may come out of the tissue tunnel 500 with the removal of trephine 220. Additional instruments, suction, and/or the like may be used to remove any remaining pieces of bone or cartilage from the tissue tunnel 500.

FIG. 8A is a perspective view from a lateral viewpoint of the proximal tibia 400 shown in partial cross section, with the trial shaft 370 and a trial tip 800, attached to the trial shaft 370, placed through the bone port 230. The trial tip 800 may be one of the trial tips 320, angled at 45°. As shown, the trial tip 800 may be positioned and oriented such that the trial tip distal end 324 is positioned to match the surface topography of the surrounding cartilage and/or bone around the repair site. The trial shaft outer diameter 376 may be approximately 10 mm to provide for a close sliding fit inside the bone port inner diameter 233. The trial shaft 370 with an attached trial tip such as the trial tip 800 is also referred to herein as a "trial."

The trial tip 800 shown in FIG. 8 has a surface 810 on the trial tip distal end 324 that is a plane at a 45-degree angle to the bone port longitudinal axis 235. Users can select from a plurality of trial tips (for example, from the trial tips 320 of FIG. 3) to find the trial tip with a trial tip distal end that is most conformal to the topography of the surrounding cartilage and/or bone. Some trial and error may be needed. In addition to the depth markings 379, the trial shaft 370 and/or the trial tip 800 have one or more trial timing marks 820 that are used to indicate the circumferential orientation of the trial relative to the bone port 230 as measured against the one or more circumferential timing marks, such as the orientation markings 239 of the bone port 230. As shown in FIG. 8, the circumferential orientation is approximately 55 degrees.

The depth markings 379 of the trial shaft 370 may be measured against the bone port o proximal end 232 to indicate the depth that the trial tip 800 extends beyond the entry hole into the tissue tunnel 500, thus allowing measurement of the length of the tissue tunnel 500 when the trial tip distal end 324 is flush with the surrounding cartilage surface. As shown in FIG. 8A, the length of the tissue tunnel 500 is approximately 35 mm. The circumferential orientation and the length may be noted by the user in preparation for future steps.

FIG. 8B is a perspective view from a lateral viewpoint of the proximal tibia 400 shown in partial cross section and a trial shaft 370 with an attached angled trial tip 800 placed through a bone port 230 and with the trial tip distal end 324 positioned to match the surface topography of the surrounding cartilage and/or bone. An optional orientation storage feature may be coupled to the bone port proximal end 232 and used to record the orientation of the trial tip 800 when aligned with the surrounding cartilage.

More precisely, the orientation storage feature may include a dial 850 with a generally annular shape that can be rotatably coupled to the bone port proximal end 232. The dial 850 may have a pointer 852 that can be aligned, via rotation of the dial 850 on the bone port 230, with the trial timing mark 820 of the trial shaft 370. When the trial shaft 370 and the trial tip 800 are removed from the bone port 230, the dial 850 may remain in place to facilitate alignment of the bone graft with the surrounding cartilage, in a manner that matches the alignment of the trial tip 800 with the surrounding cartilage.

The dial 850 is an optional feature. It may be used in place of, or in addition to, the orientation markings 239 of the bone port 230. In some embodiments, the dial 850 may be aligned with the trial timing mark 820 as described above, and then partially removed so that the user can see which of the orientation markings 239 is aligned with the pointer 852. This orientation may then be recorded for future use without requiring further use of the dial 850.

After performance of the steps illustrated in FIG. 8A and/or FIG. 8B, removal of the damaged and/or diseased tissue from the proximal tibia 400 may be complete. All information needed to prepare the replacement tissue may have been obtained. Thus, the user may proceed to prepare the replacement tissue, as will be shown and described in connection with FIGS. 9A through 11. Advantageously, the bone port 230 may remain attached to the tissue tunnel 500 during preparation of the replacement tissue to facilitate the subsequent insertion of the replacement tissue into the graft site.

FIG. 9A is a perspective view showing the base 330 (with assembled insert, if applicable) next to the trial tip 800 connected to the trial shaft 370. The base 330 may releasably attach to the trial tip proximal end 322 such that the trial tip distal end 324 faces away from the base 330. The base 330 may also releasably attach to the delivery tube distal end 354, for example, at or around the plateau 334. The base 330 may have a base timing mark 900 that aligns with the trial timing mark 820 on the trial tip 800 when the trial tip 800 is assembled to the base 330.

FIG. 9B is the view of FIG. 9A showing the transfer of the trial tip 800 from the trial shaft 370 to the base 330. The trial tip 800 may releasably connect to each of the trial shaft 370 and the base 330 by sliding the trial tip 800 in from the side of the trial shaft 370 and base 330, respectively, such that the slot 327 receives the slider 377 of the trial shaft 370 or the slider 337 of the base 330. However, any other releasable connection feature that resists dislodgement during use may be substituted for the slot 327, the slider 377, and the slider 337.

FIG. 10A is a perspective view showing the delivery tube 350 attached to the base 330 with the tamp 240 positioned in the delivery tube 350. The delivery tube 350 has a delivery tube timing mark 1000 and a delivery tube depth scale 1010. The delivery tube depth scale 1010 and/or the circumferential grooves 249 can be referenced to create a graft having the same length as the previously measured length of the tissue tunnel 500. When assembled to the base 330, the delivery tube timing mark 1000 and the trial timing mark 820 may be aligned with the base timing mark 900. If desired, one of the circumferential grooves 249 may be replaced with a reference line 1030 to show a preferred depth of insertion of the tamp 240.

FIG. 10B is a close-up view of FIG. 10A with the delivery tube 350 cut away to show bone graft material compacted proximally by a tamp 240 and distally by the trial tip 800 used to simulate repair of the osteochondral lesion 410 in FIG. 8 to form a formed end on the compacted bone graft 1020 corresponding to the trial tip distal end 324 of the trial tip 800. High forces, typically generated by strikes from a surgical mallet, may be applied (for example, to the handle 247 of the tamp 240) to fully compact the bone graft material to form the compacted bone graft 1020.

FIG. 11 is a perspective view in partial cross-section of the trial shaft 370 and the delivery tube 350, showing cartilage graft material 1100 compacted into the delivery tube distal end 354 distally by the trial tip 800 with trial shaft 370 attached, thereby fabricating a stratiform osteochondral graft 1110 with a formed end 1120, having the cartilage graft material 1100, that corresponds to the shape of the trial tip distal end 324 of the trial tip 800. Alternatively, trial tip 800 could be attached to base 330 (of FIGS. 9A through 10B) to shape cartilage graft material 1100. The trial timing mark 820 and the delivery tube timing mark 1000 may be maintained in alignment during the compaction process. The delivery tube timing mark 1000 and/or the depth markings 379 of the trial shaft 370 may again be used to ensure that the stratiform osteochondral graft 1110 has the appropriate length to match the length of the tissue tunnel 500.

Compaction may be performed under light force, typically generated by hand pressure, to avoid compromising the biological viability of the cartilage graft material 1100. The method of compacting the bone graft material under high force (described above in connection with FIGS. 10A and 10B) as a distinct and separate step from compacting the cartilage graft material under low force is advantageous for fabricating the stratiform osteochondral graft 1110 that has sound structural properties and cohesiveness while preserving the biological viability of the more delicate biological components of the cartilage graft material 1100.

It is advantageous to fabricate a stratiform osteochondral graft 1110 from constituent graft materials for several reason. First, the use autograft or allograft osteochondral plugs can be avoided when desired. The former has risk of harvest site morbidity, and the latter has risk of availability, immunological reactions, and disease transmission. Furthermore, the stratiform osteochondral graft 1110 can be created layer by layer, allowing the selection of the graft material that has the highest potential to remodel and heal into the same tissue constituency and structure as normal osteochondral tissue. For example, normal osteochondral tissue presents with the following distinct biological zones: 1) a cartilage surface layer, where elongate cartilage cells are arranged with their long axes parallel to the surface, 2) a cartilage transition layer, 3) a cartilage deep layer, where elongate cartilage cells are arranged with their long axes perpendicular to the surface, 4) a demarcation layer called the tidemark, 5) a calcified cartilage layer, and 6) a subchondral bone layer. Optimal graft materials can be selected to optimally reproduce the biological constituency and structure of each of these biological layers. A list of graft materials for cartilage and bone is provided below.

The bone graft material may be selected from a group consisting of autograft bone, allograft bone, xenograft bone, demineralized bone matrix, bone graft substitutes, extracellular matrix, bone cells, growth factors, blood derivatives, bone marrow aspirate, synthetic bone, and combinations thereof. Bone graft substitutes may be selected from a group consisting of: tricalcium phosphates, hydroxyapatites, calcium phosphates, calcium sulfates, bioglasses, collagen, and combinations thereof. Extra cellular matrix may be selected from a group consisting of proteoglycans (including heparan sulfate, chondroitin sulfate and keratan sulfate), hyaluronic acid, collagen, elastin, fibronectin, laminin. Bone cells may be selected from the group consisting of osteocytes, osteoblasts, mesenchymal stem cells, embryonic stem cells, and combinations thereof. Growth factors may be selected from a group consisting of transforming growth factor (TGF), bone morphogenic protein (BMP), insulin-like growth factor (IGF), vascular endothelial growth factor (VEGF), platelet-derived growth factor (PDGF), fibroblast growth factor (FGF), hepatocyte growth factor (HGF), and combinations thereof. Blood derivatives may be selected from a group consisting of whole blood, platelet rich plasma, and combinations thereof.

Cartilage graft material may be selected from a group consisting of autograft cartilage, allograft cartilage, xenograft cartilage, extracellular matrix, tissue scaffolds, cartilage cells, cell sheets, biological glues, growth factors, blood derivatives, bone marrow aspirate, synthetic cartilage, or combinations thereof. Cartilage cells are selected from a group consisting of chondrocytes, chondroblasts, mesenchymal stem cells, embryonic stem cells, and combinations thereof. Biological glues are selected from a group consisting of fibrin glue, mussel glue, vitronectin, chondronectin, osteonectin, fibronectin, laminins, arginine-glycine-aspartic acid peptide, and combinations thereof.

Notably, autograft materials may be harvested from other locations in the body, besides the vicinity of the osteochondral lesion 410. For example, in some embodiments, a second tissue tunnel (not shown) may be formed through the proximal tibia 400 to obtain bone and/or cartilage from a different portion of the proximal tibia 400. Additionally or alternatively, tissue may be obtained from a different bone and/or joint through the use of the systems and methods set forth above.

Once the compaction process of FIG. 11 has been carried out, the stratiform osteochondral graft 1110 may be ready for placement in the graft site. One manner in which this may be accomplished will be shown and described in connection with FIGS. 12 and 13.

Figure 12:
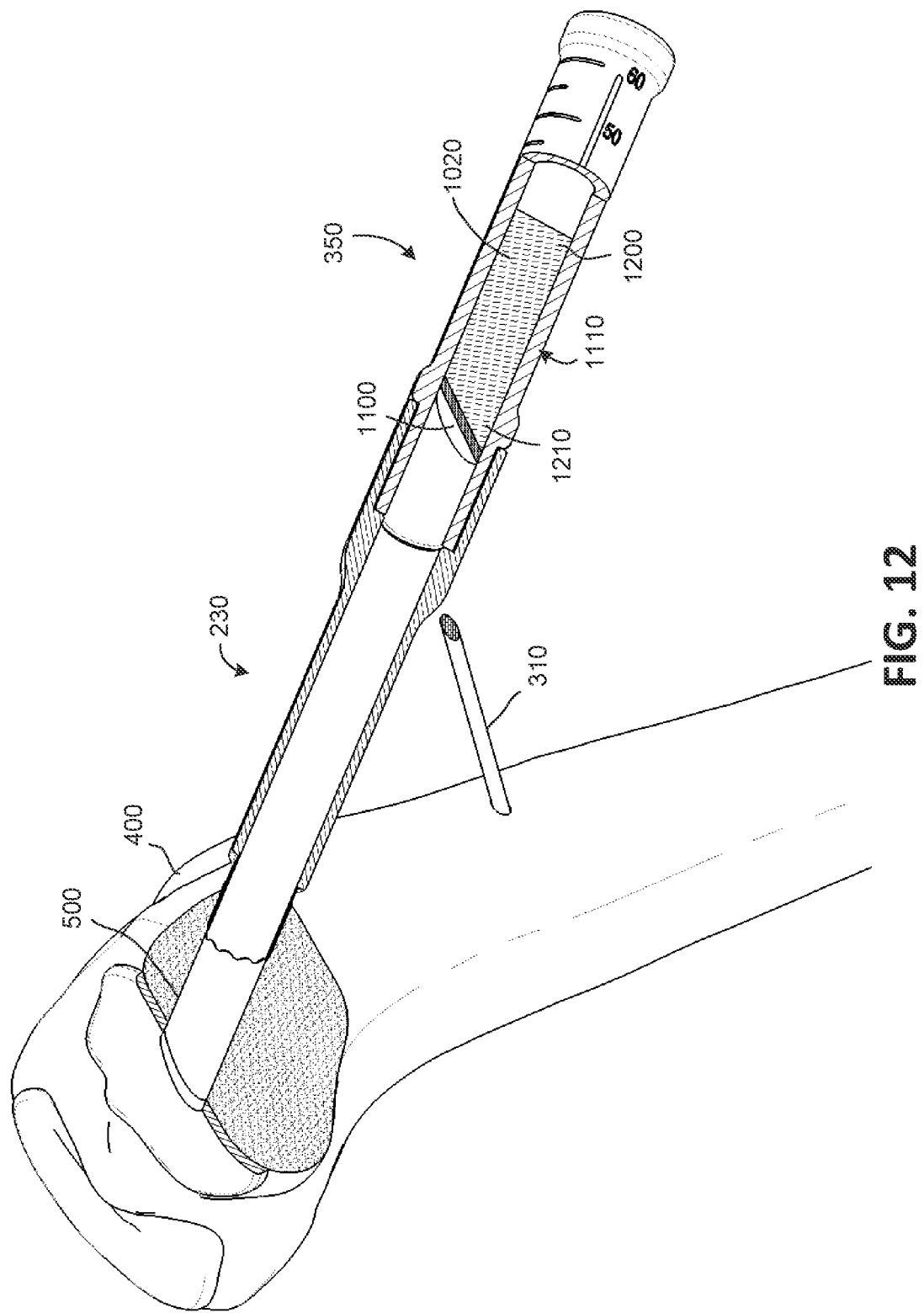
FIG. 12 is a perspective view from a lateral viewpoint shown in partial cross section of the proximal tibia showing a loaded delivery tube engaged with a bone port.

FIG. 12 is a perspective view from a lateral viewpoint shown in partial cross section of the proximal tibia 400, showing the delivery tube 350 engaged with the bone port 230. The stratiform osteochondral graft 1110 may have a graft proximal end 1200 and a graft distal end 1210. The compacted stratiform osteochondral graft 1110 may be positioned in the delivery tube 350 such that the graft distal end 1210, with the cartilage graft material 1100, is oriented toward the graft site.

Figure 13:
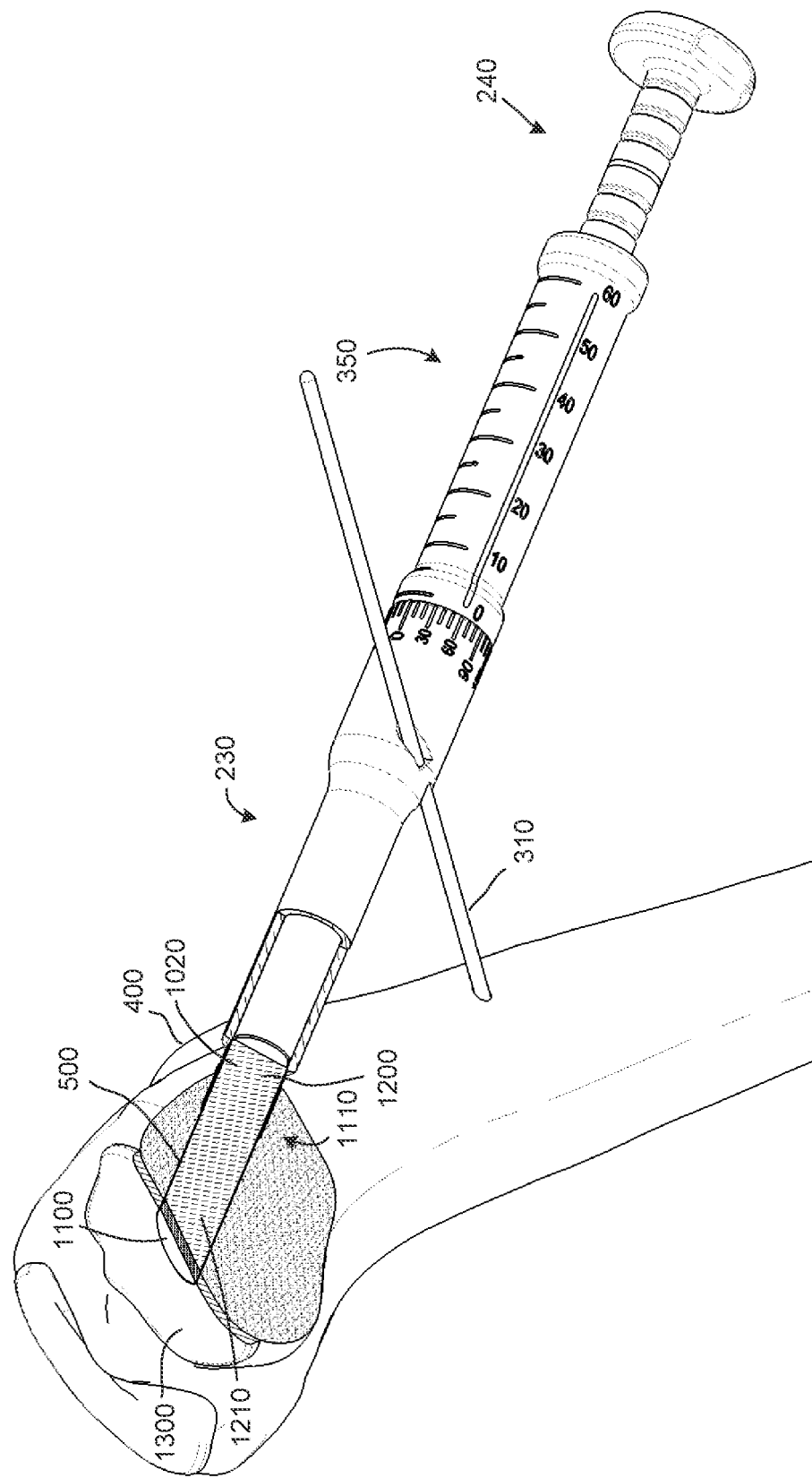
FIG. 13 is a perspective view from a lateral viewpoint shown in partial cross section of the proximal tibia shown with a tamp pushing the stratiform osteochondral graft into final position.

FIG. 13 is a perspective view from a lateral viewpoint shown in partial cross section of the proximal tibia 400, shown with tamp 240 pushing the graft proximal end 1200 so that the graft distal end 1210 is aligned with the cartilage surface 1300 at the graft site. The stratiform osteochondral graft 1110 may be moved toward the cartilage surface 1300 until the cartilage graft material 1100 is flush with the cartilage surface 1300. The bone graft 1020 may then occupy the tissue tunnel 500, proximal to the cartilage surface 1300, as shown.

Once the stratiform osteochondral graft 1110 has been positioned as shown in FIG. 13, the tamp 240, the delivery tube 350, and the bone port 230 may be removed from the proximal tibia 400. The wound site may be closed and allowed to heal. The stratiform osteochondral graft 1110 may then integrate with the surrounding tissue. For example, the cartilage graft material 1100 may integrate with the cartilage surface 1300, and the bone graft 1020 may integrate with the bone surrounding the tissue tunnel 500. The instruments of the system 300 used in the procedure may be disposed of. The instruments of the system 100 used in the procedure may be re-sterilized and prepared for use in another procedure.

In some procedures, defective tissue may be found outside the periphery of the tissue tunnel 500. In some cases, the ideal retrograde approach may not pass through all of the diseased or damaged tissue that needs to be removed. In other cases, diseased or damaged tissue outside the tissue tunnel 500 may be located (for example, endoscopically) after the tissue tunnel 500 has been formed. Curettes and/or other instruments known in the art may be inserted into the tissue tunnel 500, through the bone port 230 or directly without the bone port 230, and used to remove damaged tissue from the walls of the tissue tunnel 500. Further, in other embodiments, the systems and methods disclosed herein may be used to repair bone defects below an articular surface. In any of the above cases, the damaged tissue may be replaced with any of the materials listed previously. One method for doing this will be shown and described in connection with FIGS. 14 through 17.

Figure 14:
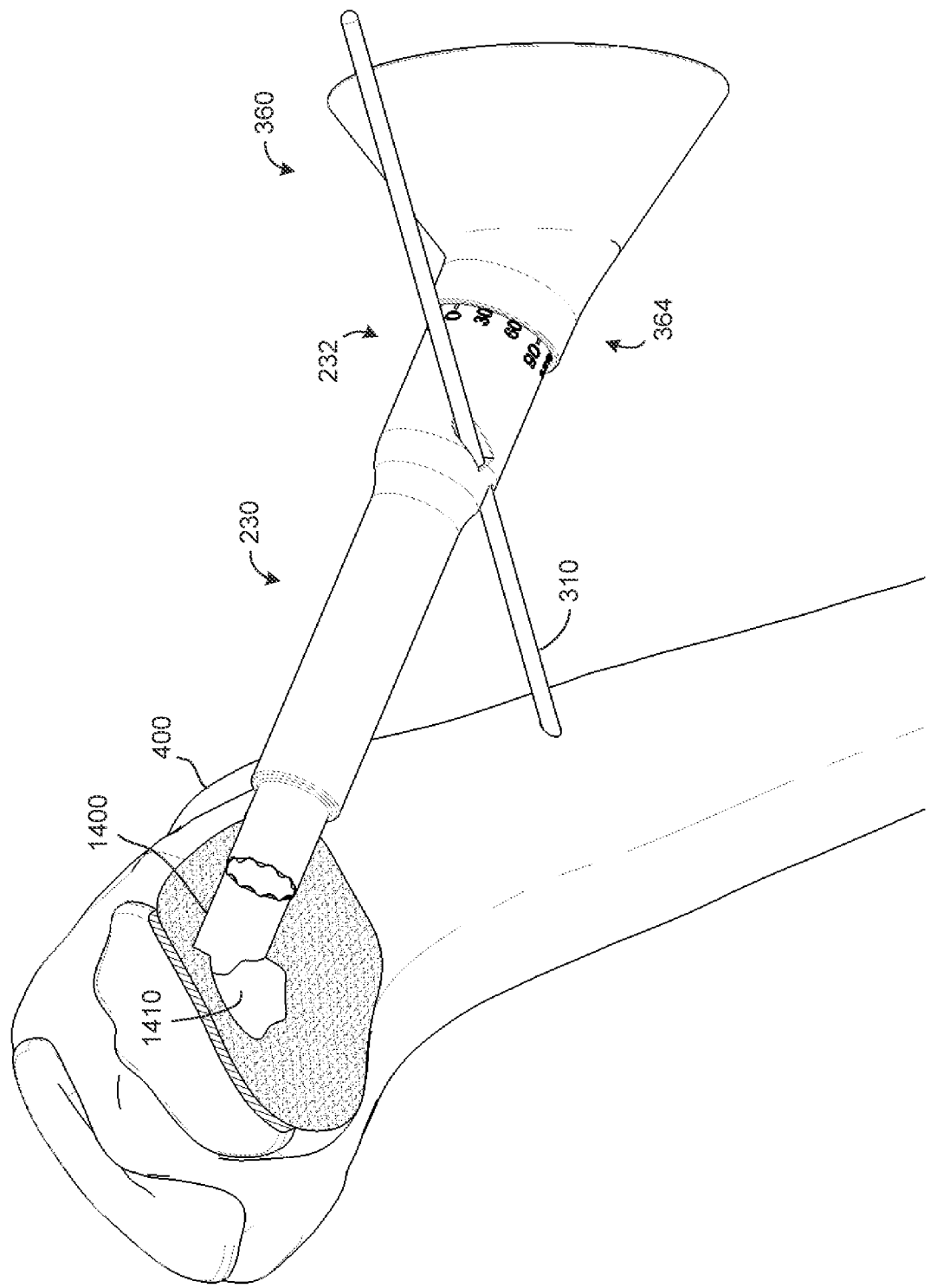
FIG. 14 is a perspective view from a lateral viewpoint shown in partial cross section of the proximal tibia with a bone port secured to the proximal tibia, an enlarged bone defect site located in the proximal tibia, and a funnel attached to the bone port.

FIG. 14 is a perspective view from a lateral viewpoint shown in partial cross section of the proximal tibia 400 with the bone port 230 secured to the proximal tibia 400 to facilitate access to a tissue tunnel 1400. An enlarged bone defect site 1410 may be located adjacent to the tissue tunnel 1400. In FIG. 14, the enlarged bone defect site 1410 may be below the articular surface of the proximal tibia 400; thus, the tissue tunnel 1400 may be a blind hole through the bone of the proximal tibia 400, that stops short of the articular cartilage. The tissue tunnel 1400 may be formed, the bone port 230 may be attached, and visualization of the tissue tunnel 1400 may be obtained substantially as set forth previously in the descriptions of FIGS. 4-7.

The funnel 360 may be attached to the bone port 230 to facilitate insertion of a tissue replacement material, such as bone graft material, into the enlarged bone defect site 1410. In particular, the funnel distal end 364 may be secured to the bone port proximal end 232 such that the funnel longitudinal axis 365 is coaxial with the bone port longitudinal axis 235. The funnel proximal end 362 may be flared to facilitate insertion of material into the funnel proximal end 362, and thence into the tissue tunnel 1400 through the funnel 360 and the bone port 230.

Alternatively, a delivery tube 350 (as shown in FIG. 3) may be used between the funnel 360 and the bone port 230.

Figure 15:
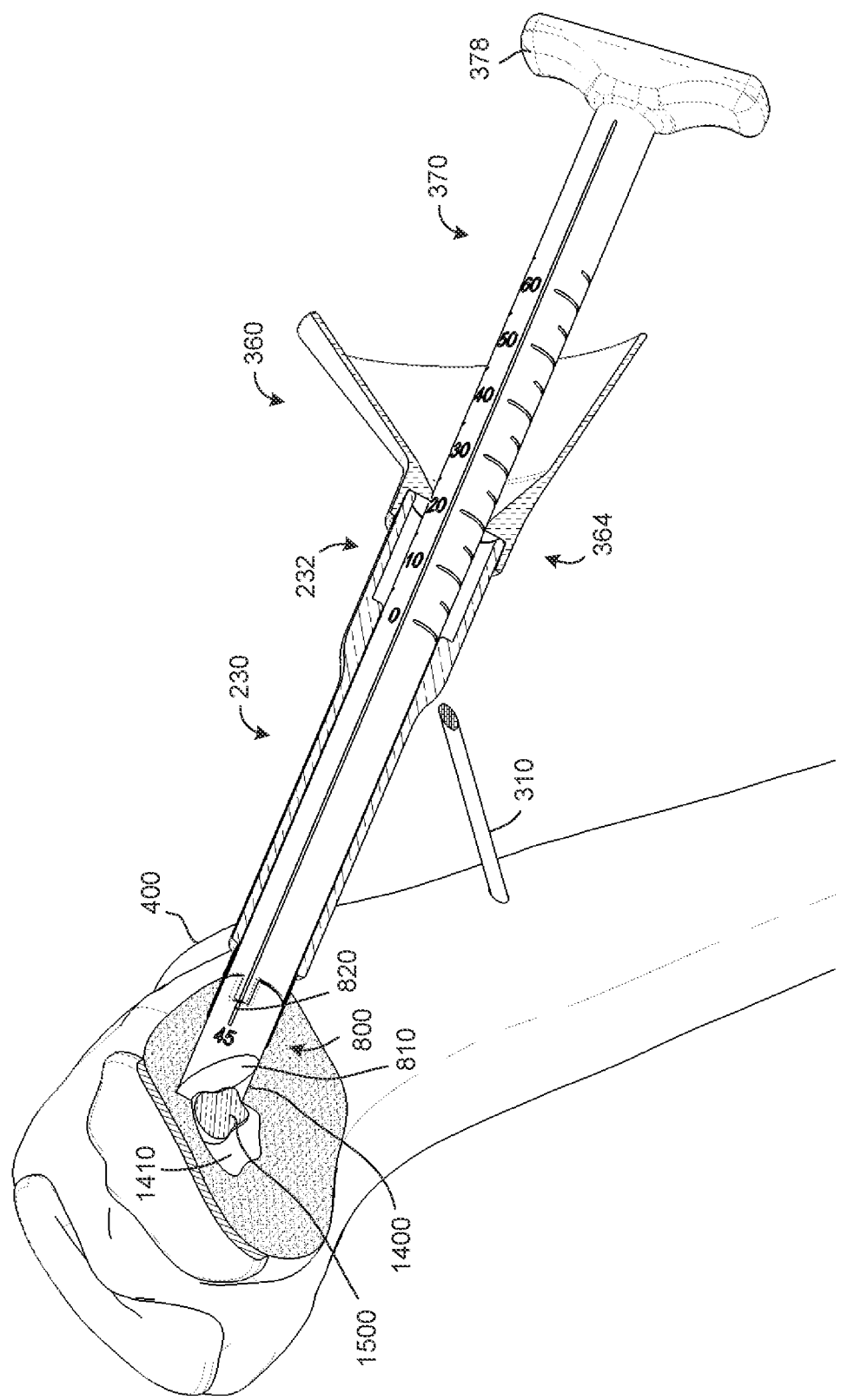
FIG. 15 is the view of FIG. 14 showing rotation and pushing of a trial to displace bone graft material into the enlarged bone defect site.

FIG. 15 is the view of FIG. 14 showing rotation and pushing of a trial to displace bone graft material 1500 into the enlarged bone defect site 1410. In this embodiment, the bone graft material 1500 may be a loose and/or uncompacted material. The trial may include the trial shaft 370 and the trial tip 800 with a trial tip distal end 324 that is angled at 45°.

The angulation of the trial tip distal end 324 may help the trial tip 800 displace the bone graft material 1500 transverse to the axis of the tissue tunnel 1400, into the enlarged bone defect site 1410. Prior to placement of the bone graft material 1500, the position of the enlarged bone defect site 1410 relative to the tissue tunnel 1400 may be assessed, for example, with medical imaging. The position may be recorded and the trial may be rotated to align the trial tip distal end 324 with the enlarged bone defect site 1410, for example, by aligning the trial timing marks 820 with the orientation markings 239 of the bone port 230. The funnel 360 is illustrated in FIG. 15 but is optional; if desired, the funnel 360 may be omitted to facilitate alignment of the trial timing marks 820 with the orientation markings 239.

After the bone graft material 1500 has been inserted into the enlarged bone defect site 1410, the bone graft material 1500 may optionally be further pressed into the enlarged bone defect site 1410. For example, a different selection from the trial tips 320 may be attached to the trial shaft 370 and advanced through the bone port 230 to further press the bone graft material 1500 into the enlarged bone defect site 1410. Alternatively a tamp 240 (as shown in FIG. 2) can be used.

Figure 16:
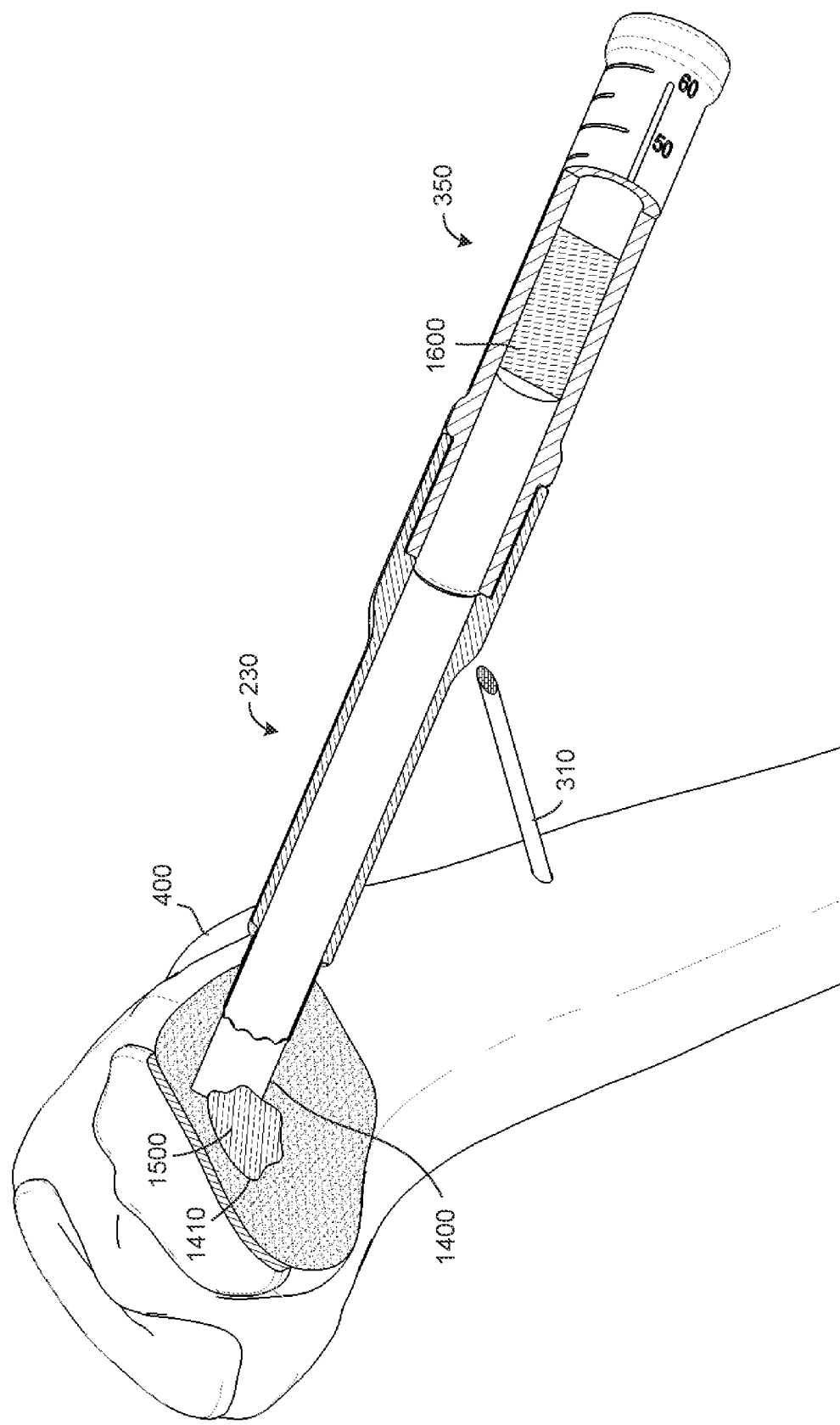
FIG. 16 is the view of FIG. 15 showing a delivery tube loaded with compacted bone graft material, with the delivery tube attached to the bone port.

FIG. 16 is the view of FIG. 15 showing a delivery tube 350 loaded with compacted bone graft material 1600. The delivery tube 350 may be attached to the bone port 230 as in FIG. 12. The compacted bone graft material 1600 may optionally include only bone, rather than being a stratiform graft, as only bone is to be replaced. The compacted bone graft material 1600 may be formed as shown and described in connection with FIGS. 9A and 9B, but may be made with a cylindrical shape rather than having an angled distal surface. Thus, one of the trial tips 320 with a trial tip distal end 324 having a perpendicular orientation and a circular shape may be attached to the base 330 in place of the trial tip 800, and used in the compaction of the bone graft 1020 to form the compacted bone graft material 1600 with the generally cylindrical shape.

Figure 17:
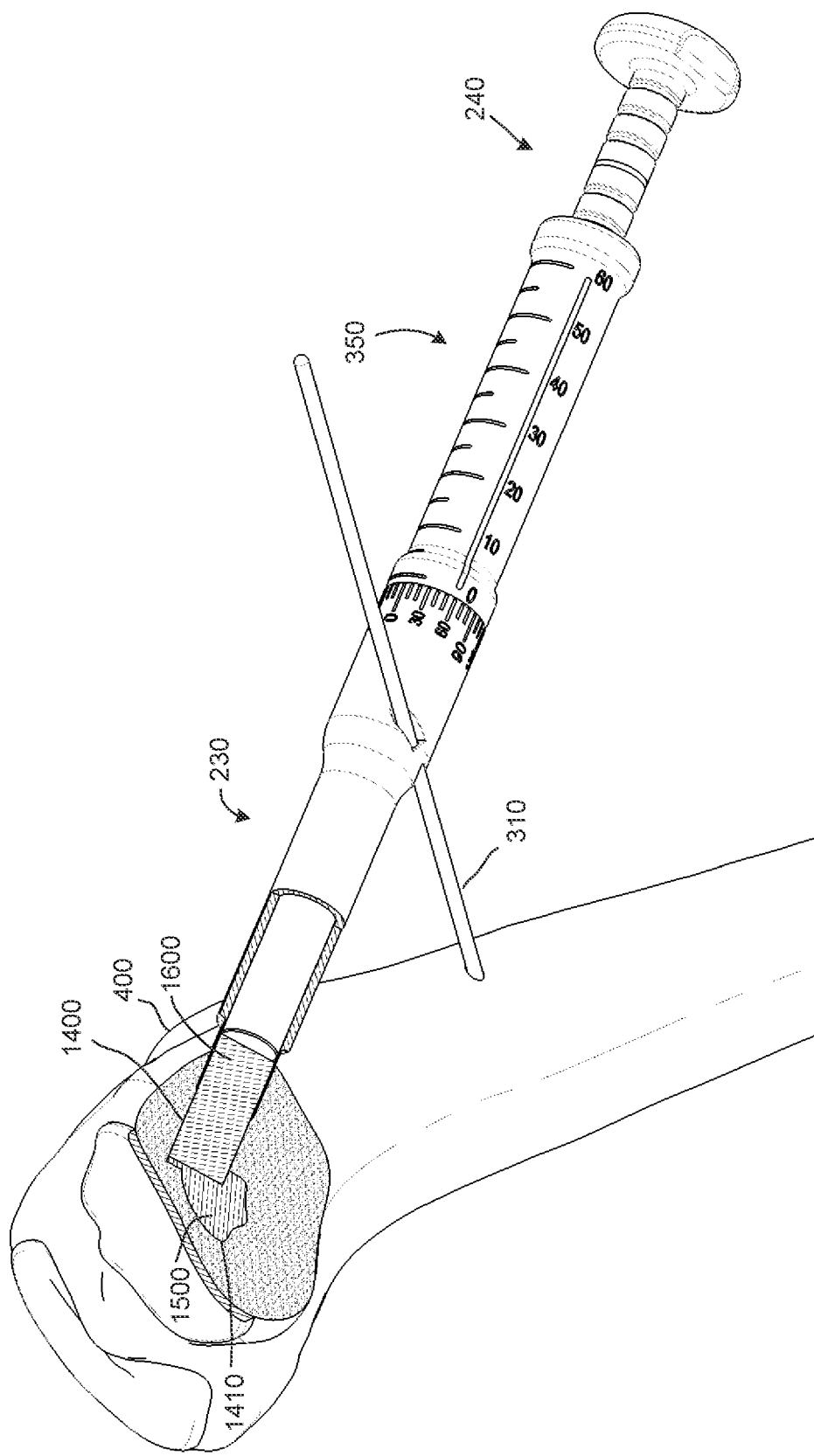
FIG. 17 is the view of FIG. 16 showing a tamp pushing the compacted bone graft into final position.

FIG. 17 is the view of FIG. 16 showing tamp 240 pushing the compacted bone graft material 1600 into final position adjacent to the enlarged bone defect site 1410. The user may rely on the "feel" (i.e., resistance to distal motion) to know when to stop pushing on the handle 247 of the tamp 240. Additionally or alternatively, medical imaging may be used to assess the location of the enlarged bone defect site 1410 relative to the tissue tunnel 1400, and the depth markings (i.e., circumferential grooves 249) of the tamp 240 may be used to push the bone graft material 1500 to the appropriate depth. Once in place, the compacted bone graft material 1600 may help retain the bone graft material 1500 in place in the enlarged bone defect site 1410, and may also fill and facilitate healing of the tissue tunnel 1400.

In addition to use of the systems and methods of the present disclosure to address tissue defects, these systems and methods may also be used to fill tissue voids resulting from bone atrophy, other surgical procedures, or prior surgical procedures that did not address the tissue void. One example of this will be presented in connection with FIGS. 18-20.

Figure 18:
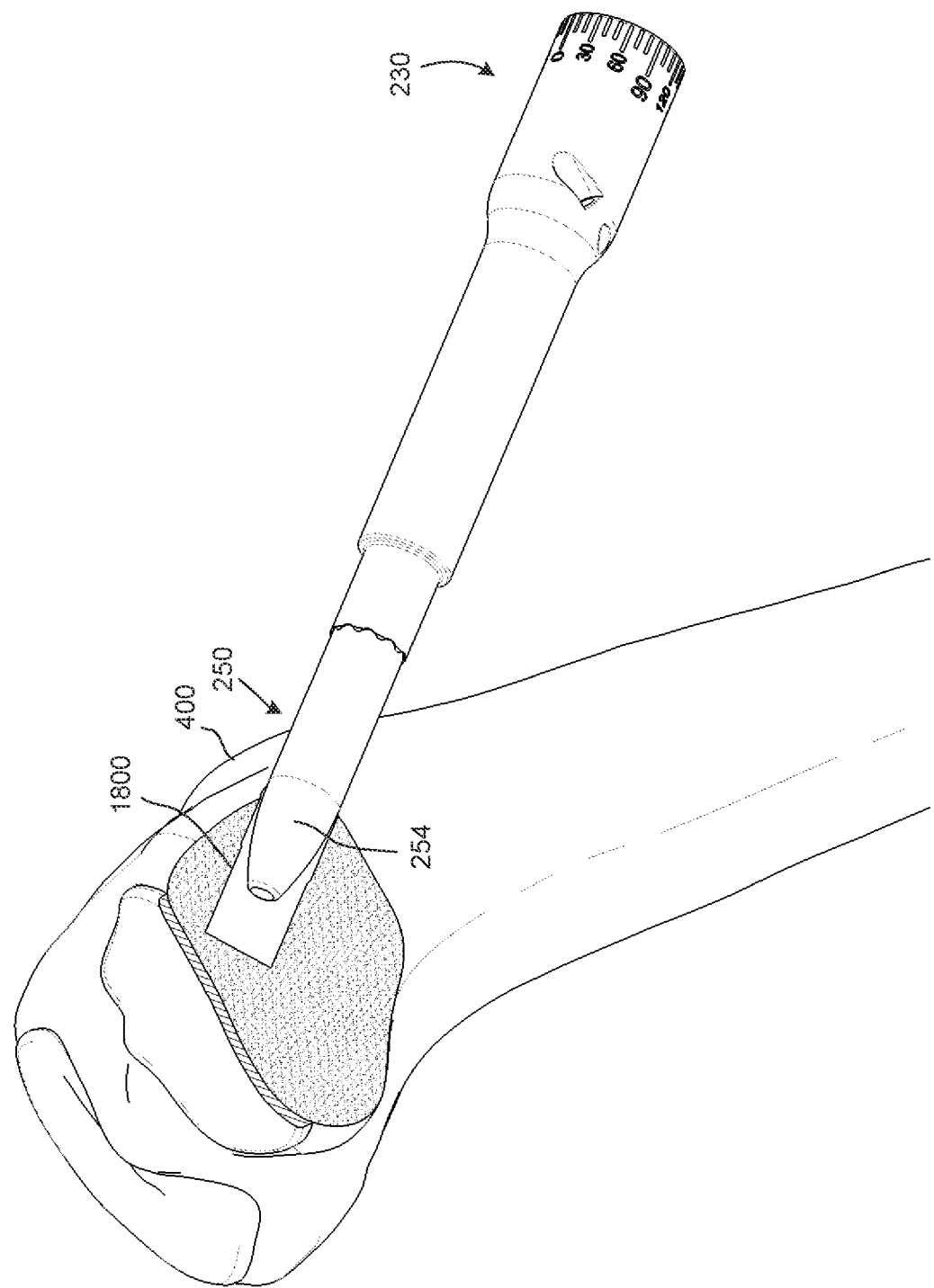
FIG. 18 is a perspective view from a lateral viewpoint shown in partial cross section of the proximal tibia with an obturator inserted into an existing bone tunnel, and a bone port placed over the obturator.

FIG. 18 is a perspective view from a lateral viewpoint shown in partial cross section of the proximal tibia 400 with obturator 250 inserted through the bone port 230. The existing tissue tunnel 1800 may be created by the user to facilitate an arthrodesis by placing compacted bone graft material across a joint, or it may be the result of a failed prior surgery, such as a tissue tunnel in a failed anterior cruciate ligament reconstruction surgery. The existing tunnel 1800 may be in the bone only, or may go all the way through the cartilage, like tunnel 500 in FIG. 7. The existing tissue tunnel 1800 may be accessed, for example, with the aid of the obturator 250, the bone port 230 may be attached, and visualization of the existing tissue tunnel 1800 may be obtained substantially as set forth previously in the descriptions of FIGS. 4-7. The obturator distal end 254 may be bullet shaped to facilitate entry into the existing tissue tunnel 1800.

Figure 19:
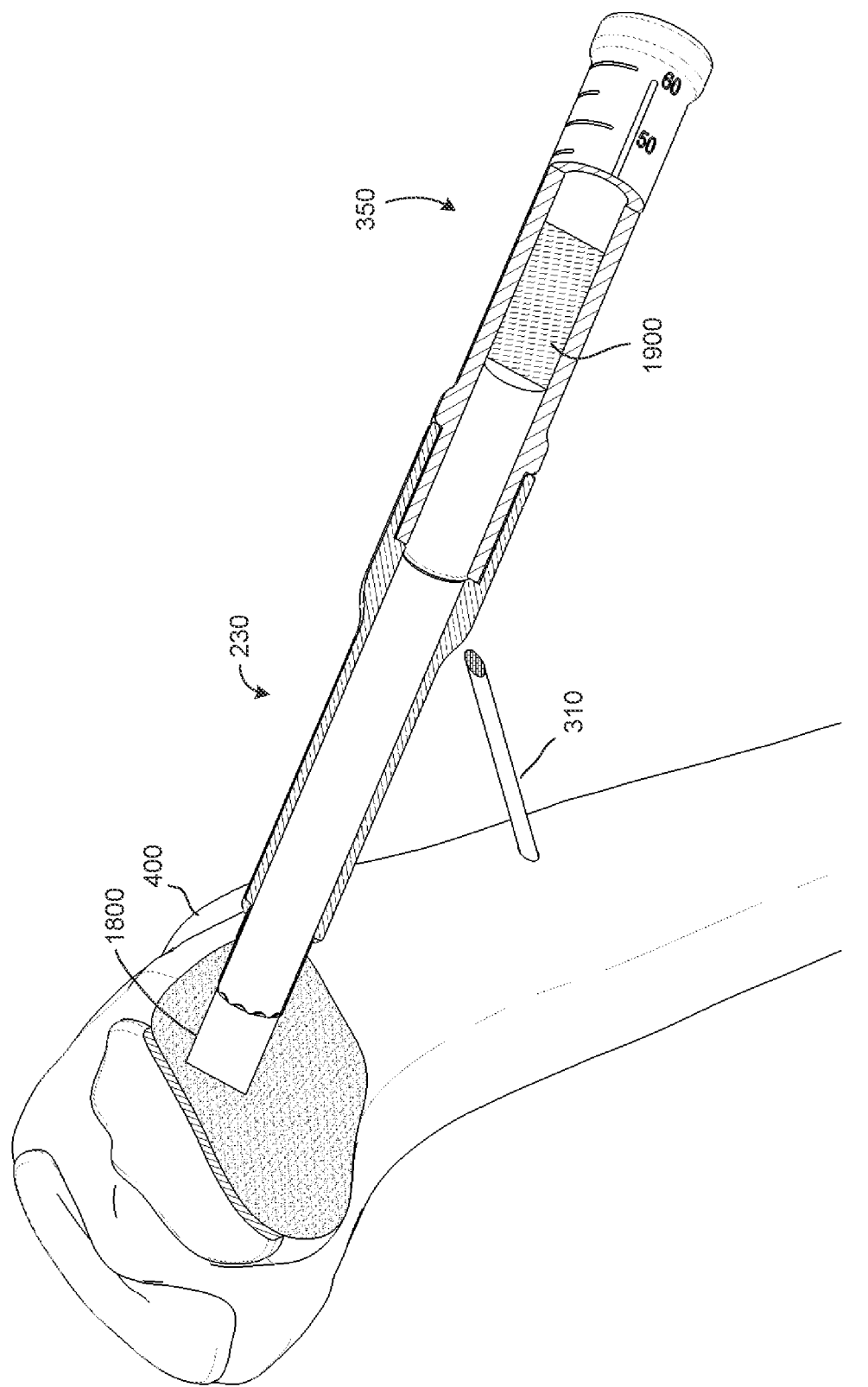
FIG. 19 is a perspective view from a lateral viewpoint shown in partial cross section of the proximal tibia with the bone port secured to the tibia, a delivery tube attached to the bone port, with the delivery tube loaded with compacted bone graft material.

FIG. 19 is a perspective view from a lateral viewpoint shown in partial cross section of the proximal tibia 400 with the bone port 230 secured to the proximal tibia 400, the delivery tube 350 attached to the bone port 230, and the delivery tube loaded with compacted bone graft material 1900. As in FIGS. 16 and 17, the compacted bone graft material 1900 may be formed, for example, as set forth in connection with FIGS. 9A and 9B, and may have a generally cylindrical shape. In alternative embodiments, the compacted bone graft material 1900 may be shaped differently to suit the shape of the portion of the existing tissue tunnel 1800 in which it is to reside.

Figure 20:
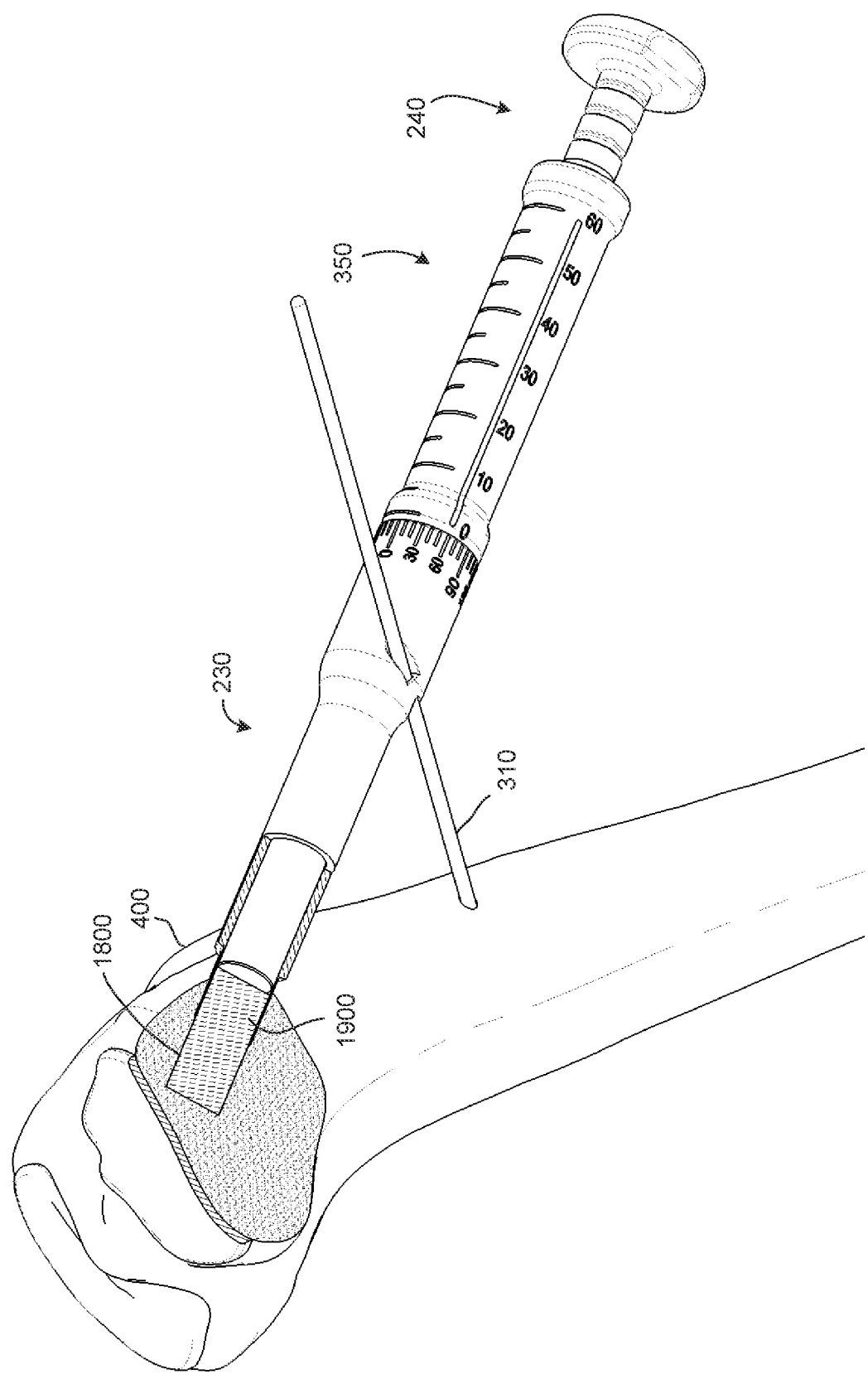
FIG. 20 is the view of FIG. 19 showing a tamp pushing the compacted bone graft material into final position.

FIG. 20 is the view of FIG. 19 showing tamp 240 pushing the compacted bone graft material 1900 into final position within the existing tissue tunnel 1800. The tamp 240 may be used to push the compacted bone graft material 1900 distally until the compacted bone graft 1900 has reached the desired location within the existing tissue tunnel 1800, which may be a blind end of the existing tissue tunnel 1800 as shown in FIG. 19.

Figure 21:
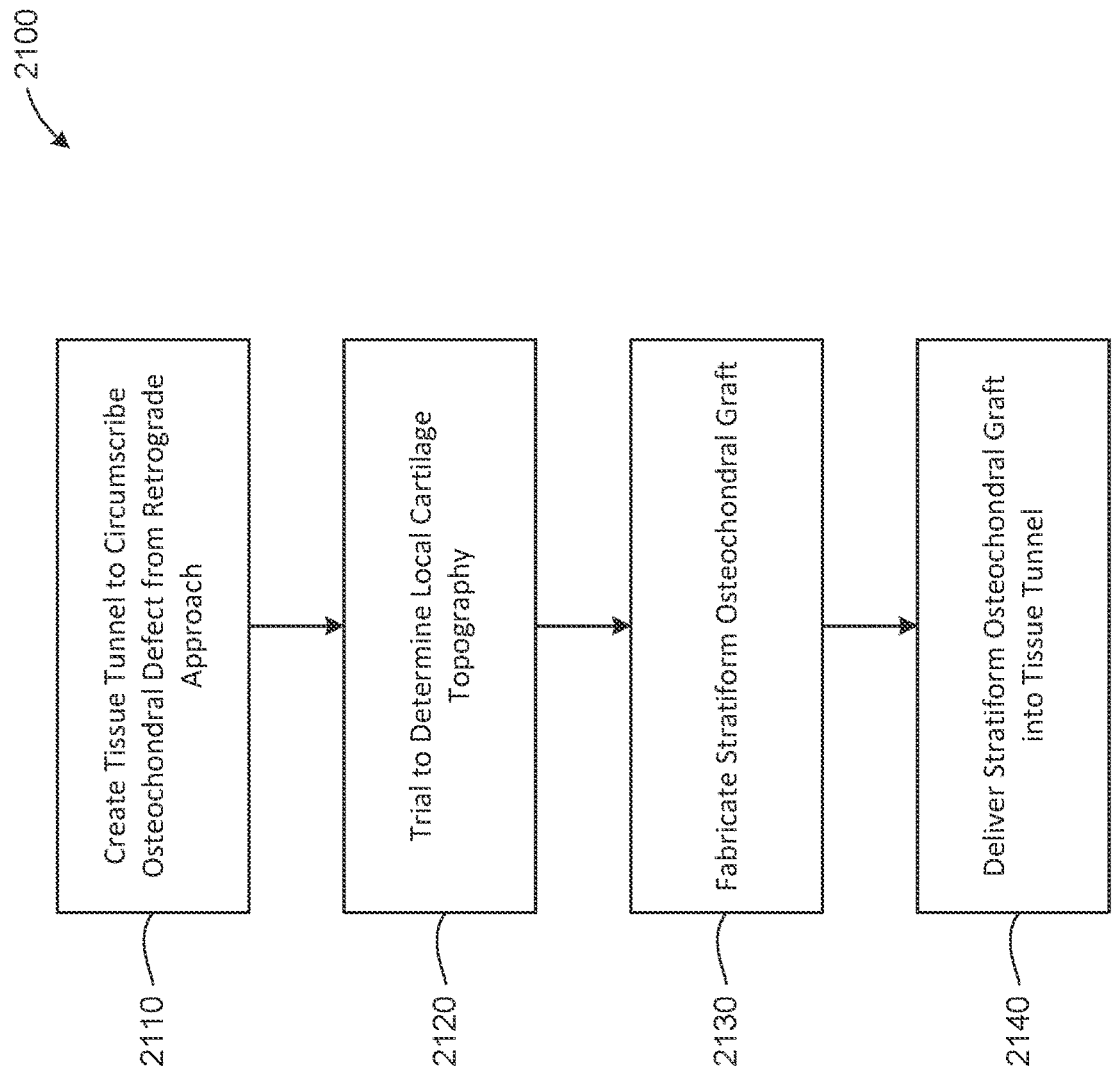
FIG. 21 is a flow chart showing a method of treating an osteochondral defect, according to one embodiment.

FIG. 21 is a flow chart showing a method 2100 of treating an osteochondral defect, according to one embodiment. The method 2100 may summarize steps that are shown and described in greater detail in FIGS. 4 through 13, and in the accompanying descriptions above.

In a step 2110, a tissue tunnel may be created to circumscribe the osteochondral defect from a retrograde approach. The step 2110 may include the procedures shown in FIGS. 4 through 7.

In a step 2120, trialing may be performed to determine the local cartilage and/or bone topography. The step 2120 may include the procedures shown in FIGS. 8A and 8B.

In a step 2130, a stratiform osteochondral graft may be fabricated. The step 2130 may include the procedures shown in FIGS. 9A through 11.

In a step 2140, the stratiform osteochondral graft may be delivered into the tissue tunnel. The step 2140 may include the procedures shown in FIGS. 12 and 13.

Figure 22:
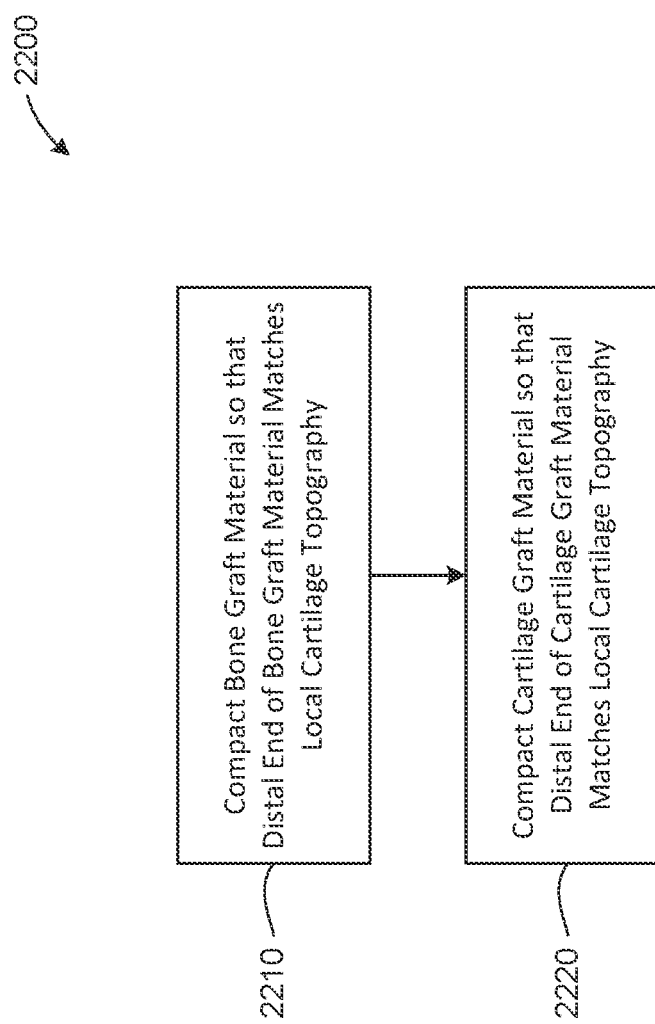
FIG. 22 is a flow chart showing a method of fabricating a stratiform osteochondral graft, according to one embodiment.

FIG. 22 is a flow chart showing a method 2200 of fabricating a stratiform osteochondral graft, according to one embodiment. The method 2200 may be a more detailed version of the step 2130 of the method 2100, and may summarize steps that are shown and described in greater detail in FIGS. 9A through 11, and in the accompanying descriptions above.

In a step 2210, bone graft material may be compacted so that the distal end of the bone graft material closely matches the local cartilage and/or bone topography. The step 2210 may include the procedures shown in FIGS. 9A through 10B.

In a step 2220, cartilage graft material may be compacted so that the distal end of the cartilage graft material closely matches the local cartilage and/or bone topography. The step 2220 may include the procedures shown in FIG. 11.

Figure 23:
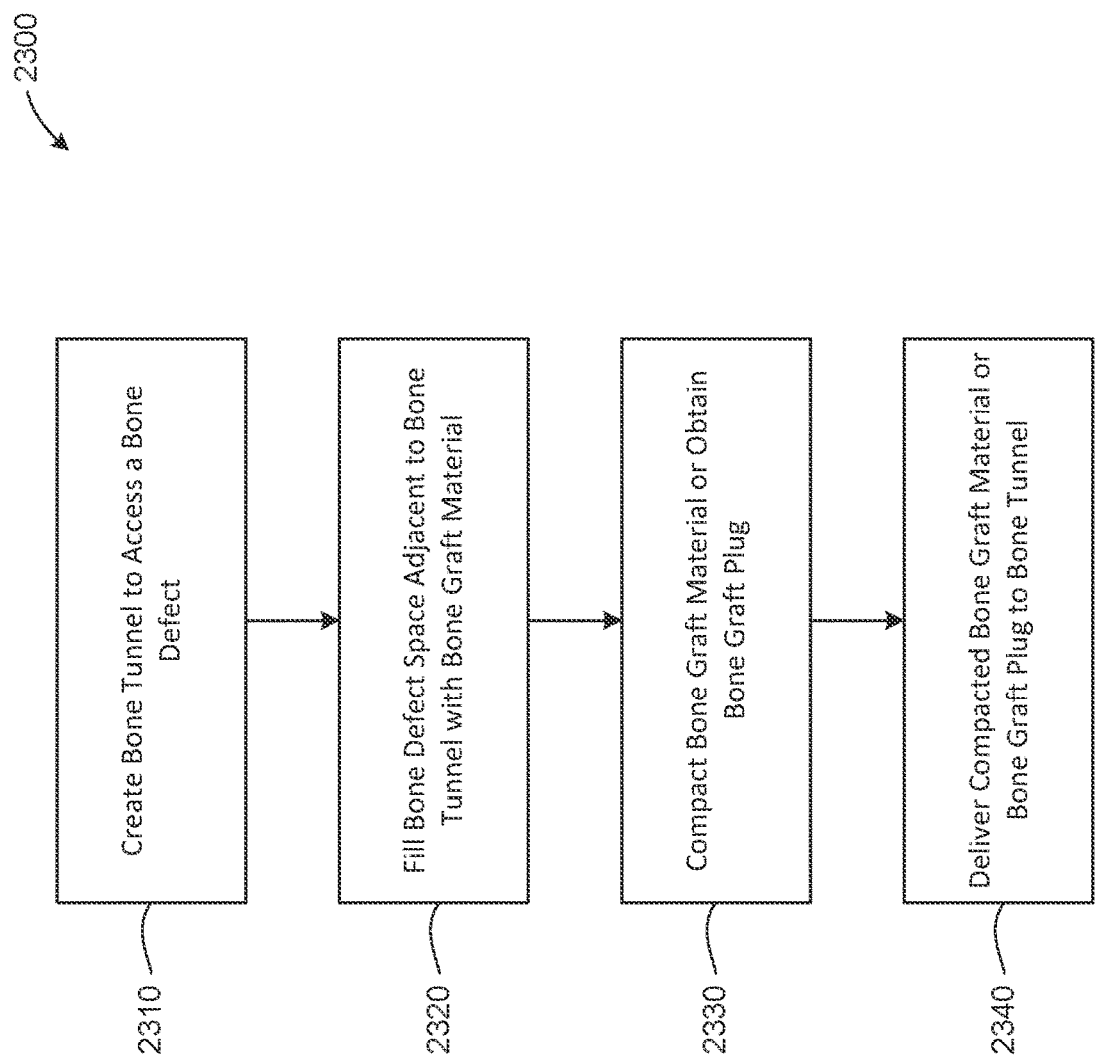
FIG. 23 is a flow chart showing a method of treating a bone defect, according to one embodiment.

FIG. 23 is a flow chart showing a method 2300 of treating a bone defect, according to one embodiment. The method 2300 may summarize steps that are shown and described in greater detail in FIGS. 14 through 17, and in the accompanying descriptions above. Steps from FIGS. 9A through 10B may also be included.

In a step 2310, a bone tunnel may be created to access a bone defect. The step 2310 may include the procedures shown in FIG. 14.

In a step 2320, a bone defect Space adjacent to the bone tunnel may be filled with bone graft material. The step 2320 may include the procedures shown in FIGS. 15 and 16.

In a step 2330, bone graft material may be compacted, or a bone graft plug may be otherwise obtained. The step 2330 may include the procedures shown in FIGS. 9A through 10B.

In a step 2340, the compacted bone graft material or the bone graft plug may be delivered to the bone tunnel. The step 2340 may include the procedures shown in FIG. 17.

FIG. 24 is a flow chart showing a method 2400 of treating an existing bone tunnel, according to one embodiment. The method 2400 may summarize steps that are shown and described in greater detail in FIGS. 18 through 20, and in the accompanying descriptions above. Steps from FIGS. 9A through 10B may also be included.

In a step 2410, an existing bone tunnel may be located with an obturator and a bone port. The step 2410 may include the procedures shown in FIG. 18.

In a step 2420, bone graft material may be compacted, or a bone graft plug may be otherwise obtained. The step 2420 may include the procedures shown in FIGS. 9A through 10B.

In a step 2430, the compacted bone graft material or the bone graft plug may be delivered to the bone tunnel. The step 2430 may include the procedures shown in FIGS. 19 and 20.

The method 2100, the method 2200, the method 2300, and the method 2400 may utilize the system 100, the subset 200, and/or the system 300. In the alternative, the method 2100, the method 2200, the method 2300, and the method 2400 may employ differently configured instruments. Likewise, the system 100, the subset 200, and/or the system 300 may be utilized in methods different from the method 2100, the method 2200, the method 2300, and the method 2400. Further, steps may be added to, omitted from, and/or replaced with alternatives in any of the method 2100, the method 2200, the method 2300, and the method 2400, as would be envisioned by a person skilled in the art.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

As used herein, the term "proximal" means a location relatively closer to a user (i.e., a surgeon) when the user is installing the implant. The term "distal" means a location relatively further from the user. For example, when a user installs a bone screw into a material with a driver, the end of the bone screw engaged with the driver is the proximal end, and the tip of the bone screw that first engages the material is the distal end. The term "cannulated" means having a central bore extending along a longitudinal axis of a part between a proximal end and a distal end of the part.

Recitation of the term "first" with respect to a feature or element does not necessarily imply the existence of a second or additional such feature or element. Elements recited in means-plus-function format are intended to be construed in accordance with 35 U.S.C. §112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A system for delivering a tissue graft to a graft site in a bone, the system comprising:
   a bone port defining a bone port longitudinal axis extending between a bone port proximal end and a bone port distal end, the bone port comprising a bone port cannulation; and
   a trial comprising:
      a trial shaft comprising:
         a trial shaft proximal end comprising a handle; and
         a trial shaft distal end insertable into the bone port cannulation;
      a trial tip configured to approximate a topography of a cartilage or bone surface; wherein:
         the bone port cannulation is sized to closely fit over the trial shaft distal end and the trial tip; and
         at least one of the bone port proximal end and the bone port distal end is securable to the bone.

2. The system of claim 1, wherein the bone port distal end is configured to be insertable into and retained in the bone.

3. The system of claim 1, further comprising a bone pin comprising a distal end insertable into the bone;
   wherein the bone port proximal end comprises a pin aperture sized to receive the bone pin to secure the bone port proximal end to the bone.

4. The system of claim 1, further comprising a delivery tube defining a delivery tube longitudinal axis extending between a delivery tube proximal end and a delivery tube distal end;
   wherein the delivery tube distal end is securable to the bone port proximal end such that the delivery tube longitudinal axis is coaxial with the bone port longitudinal axis.

5. The system of claim 1, further comprising a plurality of additional trial tips comprising:
   a first trial tip comprising a first trial tip distal surface oriented at a first angle;
   a second trial tip comprising a second trial tip distal surface oriented at a second angle different from the first angle; and
   a third trial tip comprising a third trial tip distal surface oriented at a third angle different from the first angle and the second angle.

6. The system of claim 1, wherein:
   the bone port comprises orientation markings; and
   at least one of the trial shaft and the trial tip comprises a trial timing mark that can be aligned with the orientation markings to orient the tissue graft at a predetermined orientation relative to a graft site in which the tissue graft is to be placed.

7. A system for preparing a tissue graft for insertion in a bone, the system comprising:
   a delivery tube defining a delivery tube proximal end and a delivery tube distal end;
   a tamp comprising a tamp distal end insertable into the delivery tube proximal end;
   a base securable to the delivery tube distal end; and
   a plurality of trial tips, each of which is attachable to at least one of the base and the delivery tube distal end; wherein:
      the delivery tube is sized to fit closely over the tamp distal end and each trial tip of the plurality of trial tips; and
      the plurality of trial tips comprises at least:
         a first trial tip comprising a first trial tip distal surface having a first shape;
         a second trial tip comprising a second trial tip distal surface having a second shape different from the first shape; and
         a third trial tip comprising a third trial tip distal surface having a third shape different from the first shape and the second shape.

8. The system of claim 7, wherein each of the plurality of trial tips is attachable to the base, and the base is attachable to the delivery tube distal end.

9. The system of claim 7, further comprising a bone port defining a bone port longitudinal axis extending between a bone port proximal end and a bone port distal end, the bone port comprising a bone port cannulation sized to closely fit around the tissue graft;
   wherein:
      at least one of the bone port proximal end and the bone port distal end is securable to the bone; and
      the delivery tube distal end is securable to the bone port proximal end.

10. The system of claim 9, wherein:
    the bone port comprises orientation markings; and
    the delivery tube comprises a trial timing mark that can be aligned with the orientation markings to orient the tissue graft at a predetermined orientation relative to a graft site in which the tissue graft is to be placed.

11. A system for harvesting tissue material from a body, preparing a tissue graft, and delivering the tissue graft to a graft site, the system comprising:
    a first rotary cutter defining a rotary cutter longitudinal axis extending between a rotary cutter proximal end and a rotary cutter distal end, the first rotary cutter comprising:
       a drive shaft configured to receive input torque; and
       an osteochondral cutter configured to cut tissue and receive the tissue material in response to rotation of the osteochondral cutter under pressure against the tissue; and
    a bone port defining a bone port longitudinal axis extending between a bone port proximal end and a bone port distal end, the bone port comprising a bone port cannulation;
    a delivery tube defining a delivery tube proximal end and a delivery tube distal end;
    a base securable to the delivery tube distal end;
    a trial comprising:
       a trial shaft comprising:
          a trial shaft proximal end comprising a handle; and
          a trial shaft distal end insertable into the bone port cannulation; and
       a trial tip attachable to the trial shaft distal end and configured to approximate a topography of a cartilage or bone surface; and
    a plurality of additional trial tips, each of which is attachable to the base and to the trial shaft distal end; wherein:
       at least one of the bone port proximal end and the bone port distal end is securable to a bone;
       the bone port cannulation is sized to closely fit over the trial tip and the osteochondral cutter;
       the delivery tube is sized to fit closely over the trial shaft distal end and each trial tip of the plurality of additional trial tips; and
       the plurality of additional trial tips comprises at least:
          a first trial tip comprising a first trial tip distal surface having a first shape;

a second trial tip comprising a second trial tip distal surface having a second shape different from the first shape; and a third trial tip comprising a third trial tip distal surface having a third shape different from the first shape and the second shape.

\* \* \* \* \*